(12) United States Patent
Scofield

(10) Patent No.: US 10,529,231 B2
(45) Date of Patent: Jan. 7, 2020

(54) CONDITION-BASED LANE SUGGESTIONS FOR TRAVEL ADVISING

(71) Applicant: INRIX INC., Kirkland, WA (US)

(72) Inventor: Christopher L. Scofield, Seattle, WA (US)

(73) Assignee: INRIX Inc., Kirkland, WA (US)

( * ) Notice: Subject to any disclaimer, the term of this patent is extended or adjusted under 35 U.S.C. 154(b) by 0 days.

(21) Appl. No.: 15/122,949

(22) PCT Filed: Mar. 3, 2015

(86) PCT No.: PCT/US2015/018417
§ 371 (c)(1),
(2) Date: Sep. 1, 2016

(87) PCT Pub. No.: WO2015/134444
PCT Pub. Date: Sep. 11, 2015

(65) Prior Publication Data
US 2017/0076600 A1    Mar. 16, 2017

Related U.S. Application Data

(60) Provisional application No. 61/946,962, filed on Mar. 3, 2014.

(51) Int. Cl.
*G08G 1/09* (2006.01)
*G08G 1/0967* (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC ........... G08G 1/096791; G08G 1/0112; G08G 1/012; G08G 1/0129; G08G 1/0141;
(Continued)

(56) References Cited

U.S. PATENT DOCUMENTS 6,490,519 B1 * 12/2002 Lapidot .................. G01C 21/34
340/905
6,950,504 B1    9/2005 Marx et al.
(Continued)

OTHER PUBLICATIONS

Corresponding International Application No. PCT/US15/18417, International Search report and written opinion dated Jul. 29, 2015.
(Continued)

*Primary Examiner* — Anne M Antonucci
*Assistant Examiner* — James E Stroud
(74) *Attorney, Agent, or Firm* — Cooper Legal Group, LLC

(57) ABSTRACT

Users who are traveling on a path between a first location and a second location may be informed by navigation devices about the user's selected route. The path may also feature two or more lanes, which may present comparative advantages (e.g., a toll-restricted lane may present less traffic, and a toll-free lane may present more traffic at a reduced cost). Presented herein are techniques for enabling navigation devices to advise users about the lanes of the path. A travel service may collect information about the respective lanes, such as traffic density and the typical travel duration of users utilizing the lane during various periods, and may transmit information about the predicted travel durations of the respective lanes to the device. Such information may enable the device to advise the user to choose a selected lane, according to the predicted travel durations of the lanes of the path.

20 Claims, 13 Drawing Sheets

(51) Int. Cl.
| | |
|---|---|
| H04W 4/50 | (2018.01) |
| G06N 20/00 | (2019.01) |
| G06F 16/29 | (2019.01) |
| H04W 4/024 | (2018.01) |
| H04W 4/029 | (2018.01) |
| G08G 1/01 | (2006.01) |
| B60W 40/08 | (2012.01) |
| B60W 40/09 | (2012.01) |
| G07B 15/06 | (2011.01) |
| G05D 1/00 | (2006.01) |
| G07C 5/00 | (2006.01) |
| A61B 5/0205 | (2006.01) |
| A61B 5/0476 | (2006.01) |
| A61B 5/00 | (2006.01) |
| G05D 1/02 | (2006.01) |
| H04B 1/3822 | (2015.01) |
| H04L 29/08 | (2006.01) |
| B64C 39/02 | (2006.01) |
| H04B 7/185 | (2006.01) |
| G06Q 20/10 | (2012.01) |
| G06Q 30/02 | (2012.01) |
| G08G 1/0968 | (2006.01) |
| H04W 12/08 | (2009.01) |
| H04M 15/00 | (2006.01) |
| G06Q 40/08 | (2012.01) |
| H04L 9/32 | (2006.01) |
| B60R 16/023 | (2006.01) |
| G07B 15/00 | (2011.01) |
| G08G 1/065 | (2006.01) |
| G01C 21/36 | (2006.01) |
| H04W 4/42 | (2018.01) |
| H04W 4/40 | (2018.01) |
| G01C 21/34 | (2006.01) |
| G08G 1/07 | (2006.01) |
| G08G 1/0962 | (2006.01) |
| G08G 1/0965 | (2006.01) |
| H04W 4/48 | (2018.01) |
| A61B 5/024 | (2006.01) |
| A61B 5/053 | (2006.01) |
| G06Q 50/30 | (2012.01) |

(52) U.S. Cl.
CPC ........ *A61B 5/4845* (2013.01); *B60R 16/0236* (2013.01); *B60W 40/08* (2013.01); *B60W 40/09* (2013.01); *B64C 39/024* (2013.01); *G01C 21/3469* (2013.01); *G01C 21/3617* (2013.01); *G01C 21/3655* (2013.01); *G01C 21/3667* (2013.01); *G01C 21/3682* (2013.01); *G05D 1/0011* (2013.01); *G05D 1/0088* (2013.01); *G05D 1/021* (2013.01); *G06F 16/29* (2019.01); *G06N 20/00* (2019.01); *G06Q 20/102* (2013.01); *G06Q 30/0283* (2013.01); *G06Q 40/08* (2013.01); *G07B 15/00* (2013.01); *G07B 15/063* (2013.01); *G07C 5/008* (2013.01); *G08G 1/0129* (2013.01); *G08G 1/0141* (2013.01); *G08G 1/065* (2013.01); *G08G 1/07* (2013.01); *G08G 1/093* (2013.01); *G08G 1/0962* (2013.01); *G08G 1/0965* (2013.01); *G08G 1/0967* (2013.01); *G08G 1/096725* (2013.01); *G08G 1/096741* (2013.01); *G08G 1/096775* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/024* (2018.02); *H04W 4/029* (2018.02); *H04W 4/40* (2018.02); *H04W 4/42* (2018.02); *H04W 4/50* (2018.02); *H04W 12/08* (2013.01); *A61B 5/024* (2013.01); *A61B 5/0531* (2013.01); *B60W 2040/0809* (2013.01); *B60W 2040/0872* (2013.01); *B60W 2540/22* (2013.01); *B60W 2550/12* (2013.01); *B60W 2550/14* (2013.01); *B60W 2710/1044* (2013.01); *B60W 2710/18* (2013.01); *B60W 2720/10* (2013.01); *B64C 2201/123* (2013.01); *G01C 21/3608* (2013.01); *G06Q 50/30* (2013.01); *G06Q 2240/00* (2013.01); *H04W 4/48* (2018.02)

(58) Field of Classification Search
CPC ...... G08G 1/0145; G08G 1/07; G08G 1/0962; G08G 1/0965; G08G 1/0967; G08G 1/096811; G08G 1/096822; G08G 1/096838; G08G 1/097; G08G 1/065; A61B 5/02055; A61B 5/0476; A61B 5/4845; A61B 5/024; A61B 5/0531; B60R 16/0236; B60W 30/143; B60W 2710/1044; B60W 2710/18; B60W 2710/10; B64C 39/024; B64C 2201/123; G01C 21/3415; G01C 21/3469; G05D 1/0011; G05D 1/0088; G05D 1/021; G06F 17/30241; G06N 99/005; G06Q 20/102; G06Q 50/30; G06Q 2240/00; G07B 15/00; G07B 5/008; C06Q 40/08; H04B 1/3822; H04B 7/18504; H04L 9/3247; H04L 67/02; H04L 67/306; H04M 15/60; H04W 4/001; H04W 4/046; H04W 12/08; C60Q 30/0283
USPC ....................................................... 701/421
See application file for complete search history.

(56) References Cited

U.S. PATENT DOCUMENTS

| | | | |
|---|---|---|---|
| 2010/0063715 A1 | 3/2010 | Wynter et al. | |
| 2010/0228467 A1* | 9/2010 | Wolfe | G08G 1/01 701/119 |
| 2013/0226668 A1* | 8/2013 | Zou | G06Q 10/04 705/7.35 |
| 2013/0282264 A1* | 10/2013 | Bastiaensen | G01C 21/3492 701/119 |
| 2016/0363455 A1* | 12/2016 | Masutani | G01C 21/3453 |

OTHER PUBLICATIONS

EP Search Report cited in EP Application No. 15758631.4 dated Nov. 7, 2017, 12 pgs.
EP Search Report cited in EP Application No. 15758631.4 dated Feb. 9, 2013, 9 pgs.

* cited by examiner

CONDITION-BASED LANE SUGGESTIONS FOR TRAVEL ADVISING

CROSS-REFERENCE TO RELATED APPLICATIONS

The present application claims priority under 35 U.S.C. § 119(e) to U.S. Patent Application No. 61/946,962, filed on Mar. 3, 2014, the entirety of which is incorporated by reference as if fully rewritten herein.

BACKGROUND

Within the field of computing, many scenarios involve devices that assist a user in navigating a vehicle, using techniques such as finding a location of interest; routing between a first location and a second location; and presenting travel-related status information, a speed limit, a traffic notification, or a warning of a hazardous weather or road condition. In many such scenarios, the device advises the user with respect to navigation; e.g., in addition to notifying the user of the presence of traffic ahead along the current route, the device may advise the user to take a different route in order to avoid such traffic. Such travel advisory systems may also utilize a variety of personal information to choose the provision of advice, such as the user's sensitivity to costs, safety, travel time, and ecological impact.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

Within navigation assistance scenarios, one factor that may be relevant to the user's navigation along a path is the selection of a lane among two or more lanes of the path. For example, a freeway along which the user is traveling may feature both a toll-controlled lane that is restricted to drivers who are willing to pay a toll, and a toll-free lane that is open to all users but may present a greater volume of traffic. While a navigation device may notify the user of the lane options for the path, and may advise the user based on the user's preferences (e.g., whether the user prefers to reduce tolls or reduce travel time), such prediction may be inaccurate if it does not take into account the current conditions of the lane. For example, a toll-restricted lane may, in the abstract, be predicted as providing faster travel along the path relative to a toll-free lane; but in some circumstances, the toll-restricted lane may provide a significant reduction of travel time, while in other circumstances, the toll-restricted lane may have a minimal, zero, or even adverse effect on travel time as compared with the toll-free lane. Many such navigation assistance devices may either not provide a recommendation to the user, or may provide a recommendation that is based on a prediction that is not informed by the current circumstances of the respective lanes of the path.

Presented herein are techniques for configuring a navigation device to assist a user who is traveling or intends to travel along a path between a first location and a second location, where the path comprises at least two lanes. In accordance with the techniques presented herein, a travel service may receive travel reports indicating travel conditions for the respective lanes of the path, and, for the respective lanes, may identify a typical travel duration. As one such example, the travel service may receive and store travel reports for the respective lanes during one or more periods (e.g., collected from users traveling the path during a first time of day, such as a morning "rush-hour" period, and also from a second time of day, such a midday period), and may identify a typical travel period for the respective lanes of the path during various periods. For a selected user who intends to travel the path during a selected period, the travel service may utilize the travel reports to identify a predicted travel duration of the respective lanes of the path, based on the typical travel durations of users who have utilized the respective lane during the period. Such evaluation may be based on upon historic data, including the stored travel reports; heuristics; human-specified information; and/or machine-learning techniques, such as an artificial neural network trained to identify a predicted travel duration for respective lanes of a path. The travel service may notify the device of the user about the travel durations of the respective paths, and/or a selected lane that is recommended for the user's intended travel along the path during the selected period.

In accordance with the techniques presented herein, the device may receive, from a travel service, a predicted travel duration of the respective lanes of the path between the first location and the second location. The device may compare the predicted travel duration of the respective lanes to identify a selected lane, and may advise the user to choose the selected lane while traveling the path between the first location and the second location.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
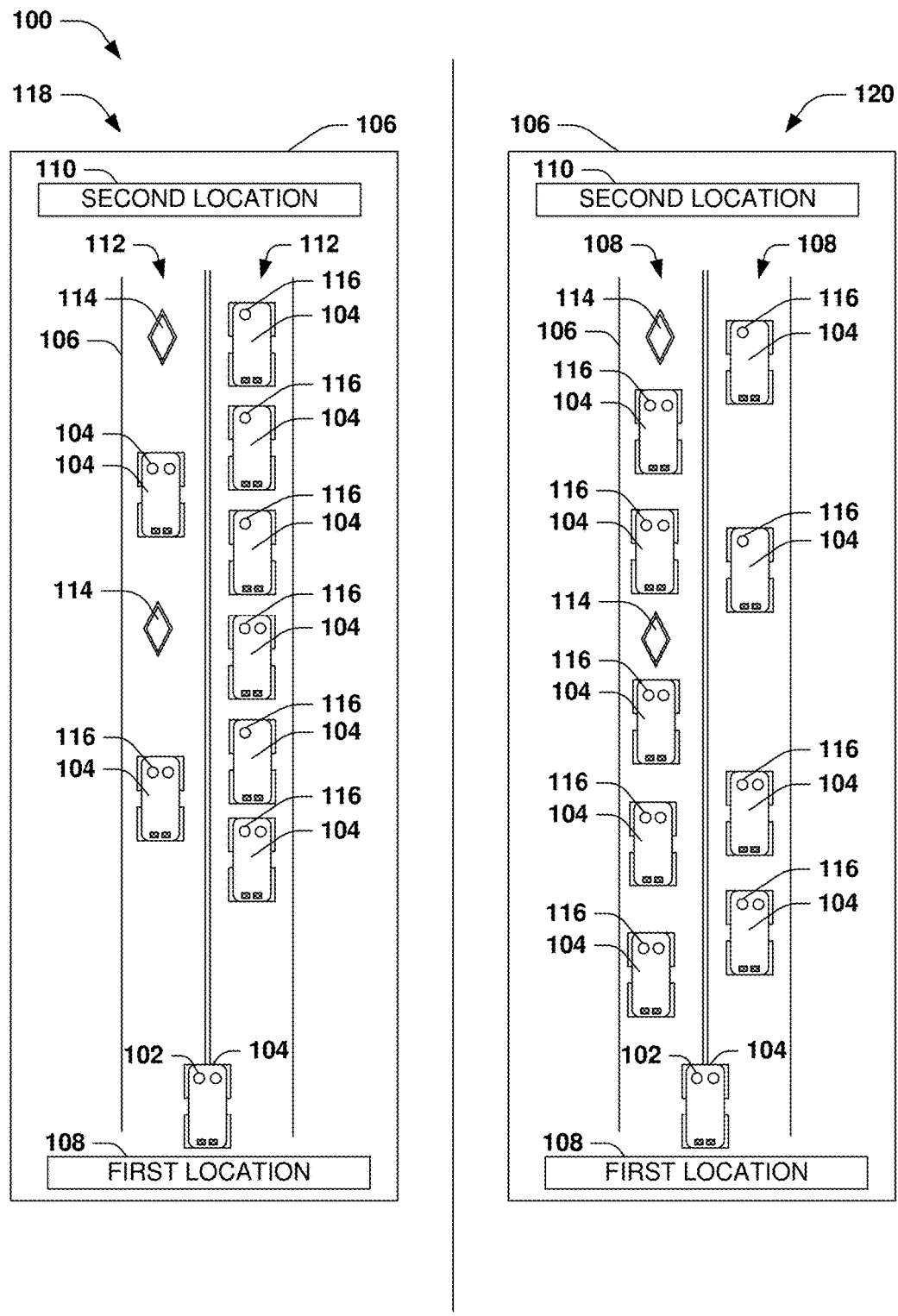
FIG. 1 is an illustration of an example scenario featuring users driving along a path from a first location to a second location.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A. Introduction

FIG. 1 is an illustration of an example scenario 100 wherein a user 102 is operating a vehicle 104 on a path 106 between a first location 108 and a second location 110. The path 106 may feature two or more lanes 112 that enable a capacity of vehicles 104 to travel on the path 106, and the user 102 may choose among the lanes 112 of the path 106 while traveling toward the second location 110. Additionally, some lanes 112 may present a travel restriction 114, such as a prerequisite toll that is assessed to the user 102 in exchange for utilizing the lane 112; a high-occupancy vehicle requirement that specifies a minimum legal occupancy of vehicles 104 using the lane 112; and/or a restriction on the speed, height, or weight of vehicles 104 using the lane 112. Other lanes 112 may present different or no travel restrictions 114, and the user 102 may be presented with a choice among the lanes 112 of the path 106.

As further illustrated in the example scenario 100 of FIG. 1, other drivers 116 who are also operating vehicles 104 of the path 106 may similarly be presented with a choice among the lanes 112, and such choices may result in different lane conditions of the respective lanes. For example, the lane restriction 114 on a first lane 112 may reduce the number of drivers 116 choosing the first lane 112, while a second lane 112 that lacks the lane restriction 114 may be more frequently selected by drivers 116. As a result, it may be projected that traffic in the second lane 112 typically exceeds traffic in the first lane 112. When faced with such a choice, the user 102 of the vehicle 104 may be compelled to compare the projected advantage of the first lane 112 and the travel restriction 114 on the first lane 112, e.g., guessing whether the possibility of faster travel along the path 106 is justified by the requirements of the travel restriction 114 of the first lane 112. For example, if the travel restriction 114 is a toll, the user 102 may choose the first lane 112 and may be willing to pay the toll when the user 102 is in a hurry; and may choose the second lane 112 to avoid the toll, despite the greater possibility of traffic and delayed travel along the path 106, when the user 102 is not in a hurry.

However, as further illustrated in the example scenario 100 of FIG. 1, the user's projection of the comparative advantages of the lanes 112 may not reflect the reality of the lanes 112 and the actual, achievable advantages thereof. For example, in a first such scenario 118, the travel restriction 114 may cause a significant reduction in traffic volume as compared with the second lane 112, and the user 102 may advantageously select the first lane 112 in order to achieve a reduced travel time. However, in a second such scenario 120, the first lane 112 may exhibit a high volume of traffic—possibly even exceeding the traffic volume of the second lane 112—and may therefore not provide a significant advantage, or may even provide a disadvantage, notwithstanding the application of the travel restriction 114 on the first lane 112. Accordingly, the user 102 may agree to be assessed a toll in order to enter the first lane 112, and may be frustrated that the first lane 112 does not provide an advantage over the toll-free second lane 112. However, the user 102 may not be capable of assessing the actual lane conditions of the respective lanes 112, e.g., due to limited vision or knowledge of the current conditions of the path 106, and may therefore have to choose a lane 112 in the absence of up-to-date information or advice.

B. Presented Techniques

Presented herein are techniques for enabling a navigation device to advise a user 102 about the choice of lanes 112 on a path 106 between a first location 108 and a second location 110, based on lane condition reports that enable a predicted travel duration if various lanes 112 of the path 106 are utilized.

Figure 2:
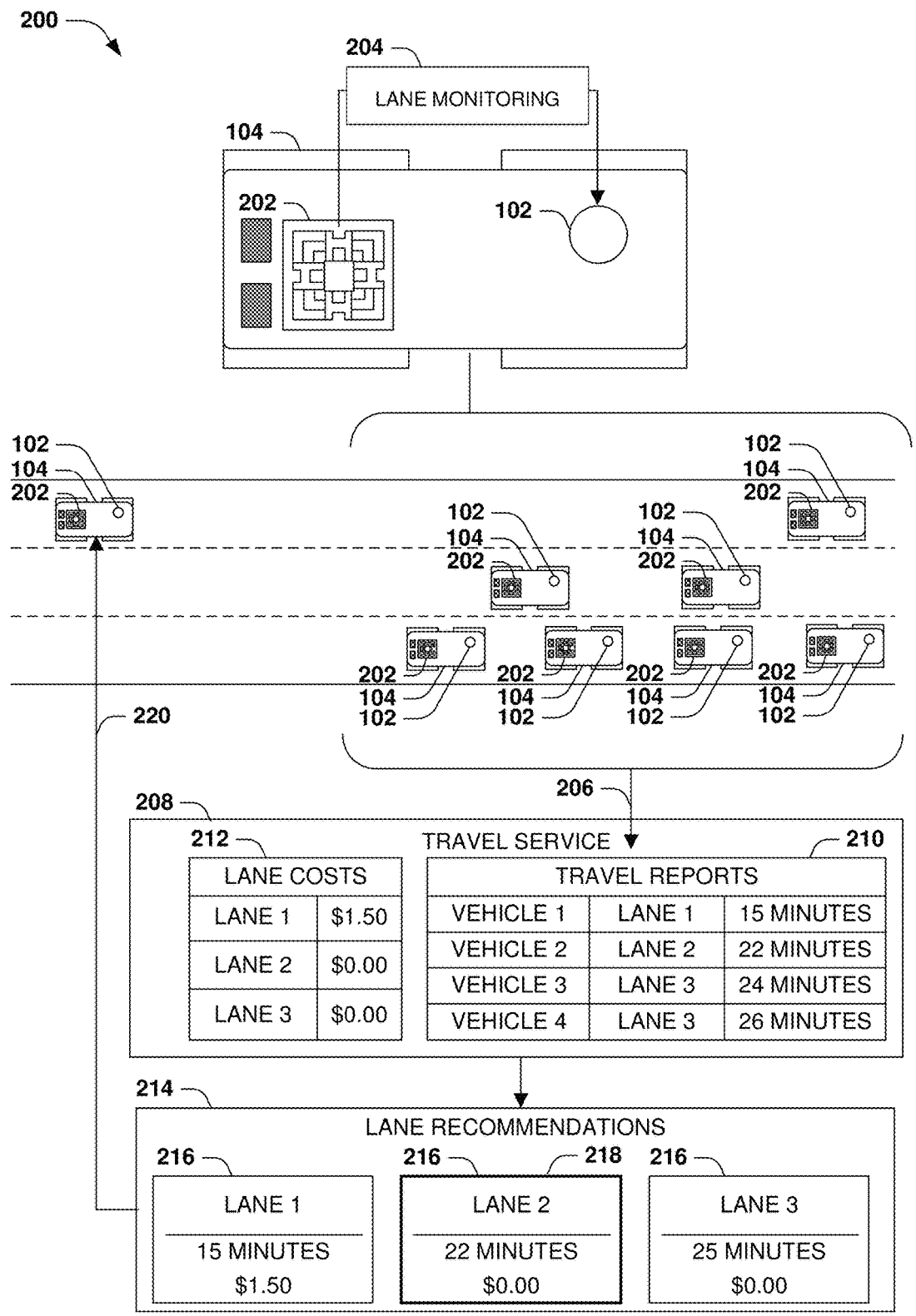
FIG. 2 is an illustration of an example scenario featuring a technique for advising a user of lane recommendations among the lanes of a path in accordance with the techniques presented herein.

FIG. 2 is an illustration of an example scenario 200 demonstrating a device 202 aboard a vehicle 102 and in communication with a travel service 208 that assists with the provision of lane recommendations. In this example scenario 200, the device 202 performs lane monitoring 204 of various lanes 112 of the path 106 between the first location 108 and the second location 110, such as traffic density in the lane 112; the speeds of vehicles 104 occupying the lane 112; and the observed travel duration between the first location 108 and the second location 110. The respective devices 202 may transmit 206 such information to a travel service 208, which may store a set of travel reports 210 submitted by the devices 202 aboard various devices 104 and respectively indicating the travel duration between the first location 108 and the second location 110 when using the lane. The travel service 208 may also compile other information 212 that is relevant to the travel service 208, such as the travel restrictions 114 (e.g., toll rates) of the respective lanes 112. According to such information, for a particular device 202 aboard a particular vehicle 104 that is traveling on the path 106 between the first location 108 and the second location 110, the travel service 208 may formulate and present a set of lane recommendations 214, respectively indicating the predicted travel duration 216 if the lane 112 is used to travel the path 106 between the first location 108 and the second location 110. The lane recommendations 214 may also be based in part on the other information 212 of the travel service 208, such as the toll rates and the travel restrictions 114 of the respective lanes 112. Additionally, the travel service 208 may provide such information 212 with the lane recommendations 214, such as the travel restrictions 214 that may affect the user's choice among the lanes 112, and/or a selected lane 218 that is recommended by the travel service 208 for the user 102. The lane recommendations are transmitted 220 to the device 202, which may advise the user 102 to choose the selected lane 218 while traveling the path 106 from the first location 108 to the second location 108, in accordance with the techniques presented herein.

C. Technical Effects

The techniques presented herein may provide a variety of technical effects in the scenarios provided herein.

As a first such example, the techniques provided herein may enable a determination of the status of a path 106, such as traffic conditions of various lanes of a road, based upon a collection of information about the lanes 112 of the path 106 from respective vehicles 104 traveling on the path 106. That is, while general traffic information about the path 106 may be derived from more generalized metrics such as the reported speeds of vehicles 104, such metrics may not provide a fully detailed account of the conditions of the respective lanes 112 of the path 106. For example, a discrepancy arising in a particular lane 112 of the path 106 as compared with the other lanes 112 of the path 106 may indicate the presence of an obstruction, such as traffic, a vehicular accident, or a pothole, which may otherwise be difficult to differentiate from a generalized traffic condition such as volume-induced congestion.

As a second such example, the techniques provided herein may enable a more detailed evaluation of the conditions of the path 106, and therefore may provide more accurate determination of routing factors, such as an estimated travel duration and an estimated time of arrival. For example, if traffic congestion is detected along the route of the user 102 between the first location 108 and the second location 110, an estimated travel duration reported to the user 102 may be updated to reflect a projected delay. The duration of the projected delay may be estimated based in part on whether the traffic congestion is confined to one of the lanes 112 of the path 106 and may therefore be avoidable, or whether the traffic congestion applies to all lanes 112 of the path 106. Additionally, the determination of the conditions of the lanes 112 of the path 106 may assist a navigation device with a determination of whether or not to re-route the user 102 through a different path 106 that may enable an avoidance of a travel delay affecting the current path 106 of the user 102.

As a third such example, the techniques provided herein may enable more detailed navigation assistance of the user 102. For example, in addition to informing the user 102 of the length of the path 106 and the lane for 112 for a projected turn or exit ramp, a navigation device that utilizes the techniques presented herein may advise the user 102, during navigation of the vehicle 104, to choose a selected lane 112 based on the travel conditions. Moreover, such information may be presented to the user 102 in a timely manner (e.g., choosing an ideal moment to advise the user 102 to select a different lane 112), and/or may be based upon current or typical conditions for the respective lanes 112 of the path 106. For example, a user 102 may be operating a vehicle 104 in a left lane 112 of the path 106, and may be embarking upon a route that involves a right turn from the right lane 112 of the path 106 two miles ahead. However, based on the evaluation of the conditions of the lanes 112 of the path 106, a navigation device may decide whether to advise the user 102 to switch to the right lane 112 as soon as possible (e.g., because traffic is developing in the left lane 112), or to remain in the left lane 112 until the turn is imminent (e.g., because traffic is developing in the right lane 112). In this manner, the navigation device may advise the user 102 in the navigation of the vehicle 104 in a manner that is informed by the current conditions of the lanes 112 of the path 106 in accordance with the techniques presented herein.

D. Example Embodiments

Figure 3:
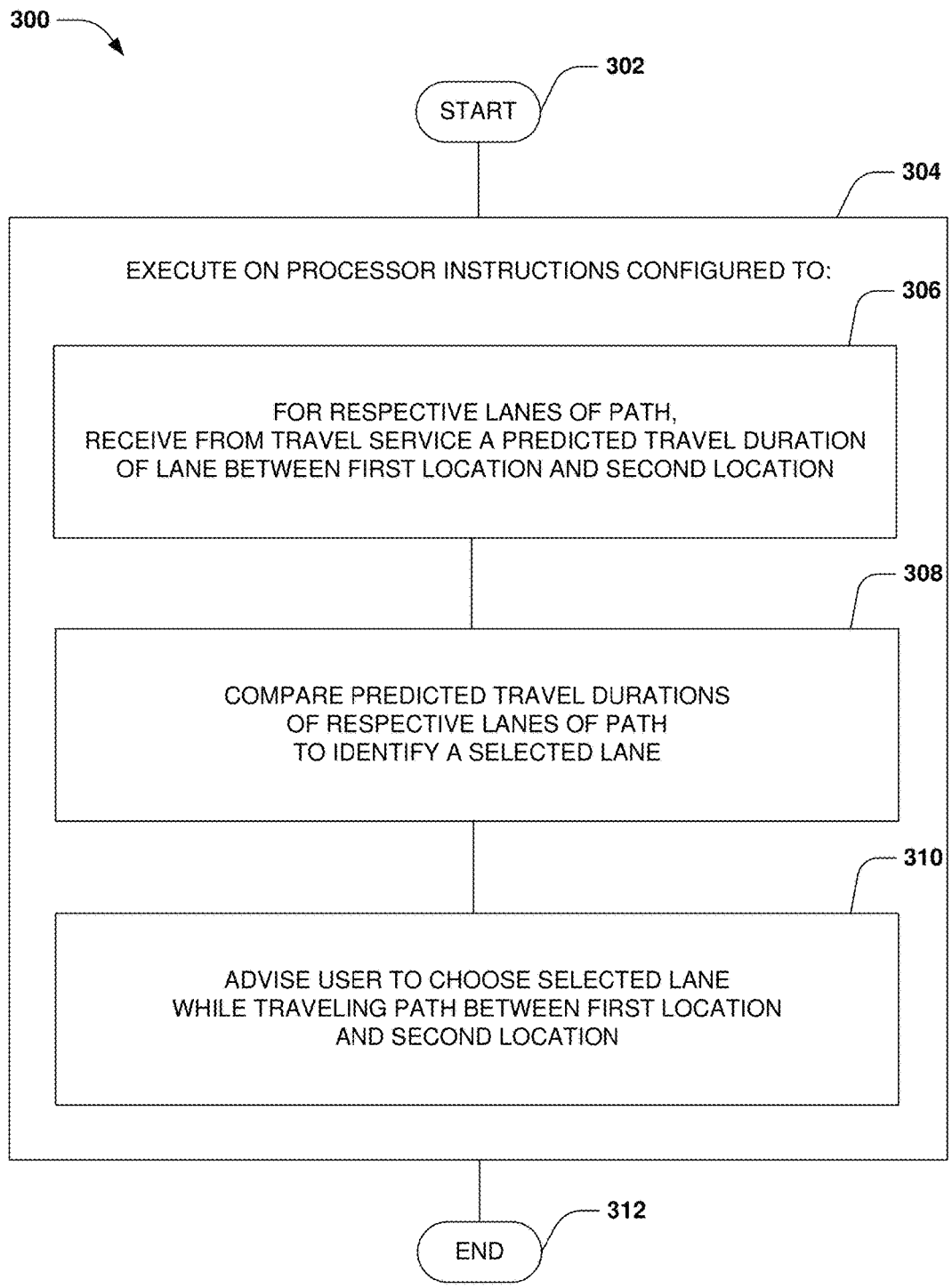
FIG. 3 is an illustration of an example method of advising a user of a selected lane, among at least two lanes of a path between a first location and a second location, in accordance with the techniques presented herein.

FIG. 3 presents a first example embodiment of the techniques presented herein, illustrated as an example method 300 of advising a user 102 operating a vehicle 104 on a path 106 having at least two lanes 112. The example method 300 may be implemented on a device having a processor, and that is in communication with a travel service 208 having information about the conditions of the lanes 112 of the path 106. The example method 300 may be implemented, e.g., as a set of instructions stored in a memory component of the device (e.g., a memory circuit, a platter of a hard disk drive, a solid-state memory component, or a magnetic or optical disc) that, when executed by the processor of the device, cause the device to perform the techniques presented herein.

The example method 300 begins at 302 and involves executing 304 the instructions on the processor. Specifically, the instructions cause the device to, for the respective lanes 112 of the path 106, receive 306 from the travel service 208 a predicted travel duration of the lane 112 between the first location 108 and the second location 110, wherein the predicted travel duration is based on a travel condition of the lane 112. The instructions also cause the device to compare 308 the predicted travel durations of the lanes 112 of the path 106 in order to identify a selected lane 218. The instructions also cause the device to advise 310 the user 102 to choose the selected lane 216 while traveling the path 106 between the first location 108 and the second location 110. In this manner, the example method 300 advises the user 102 as to the selection of lanes 112 of the vehicle 104 in accordance with the techniques presented herein, and so ends at 312.

Figure 4:
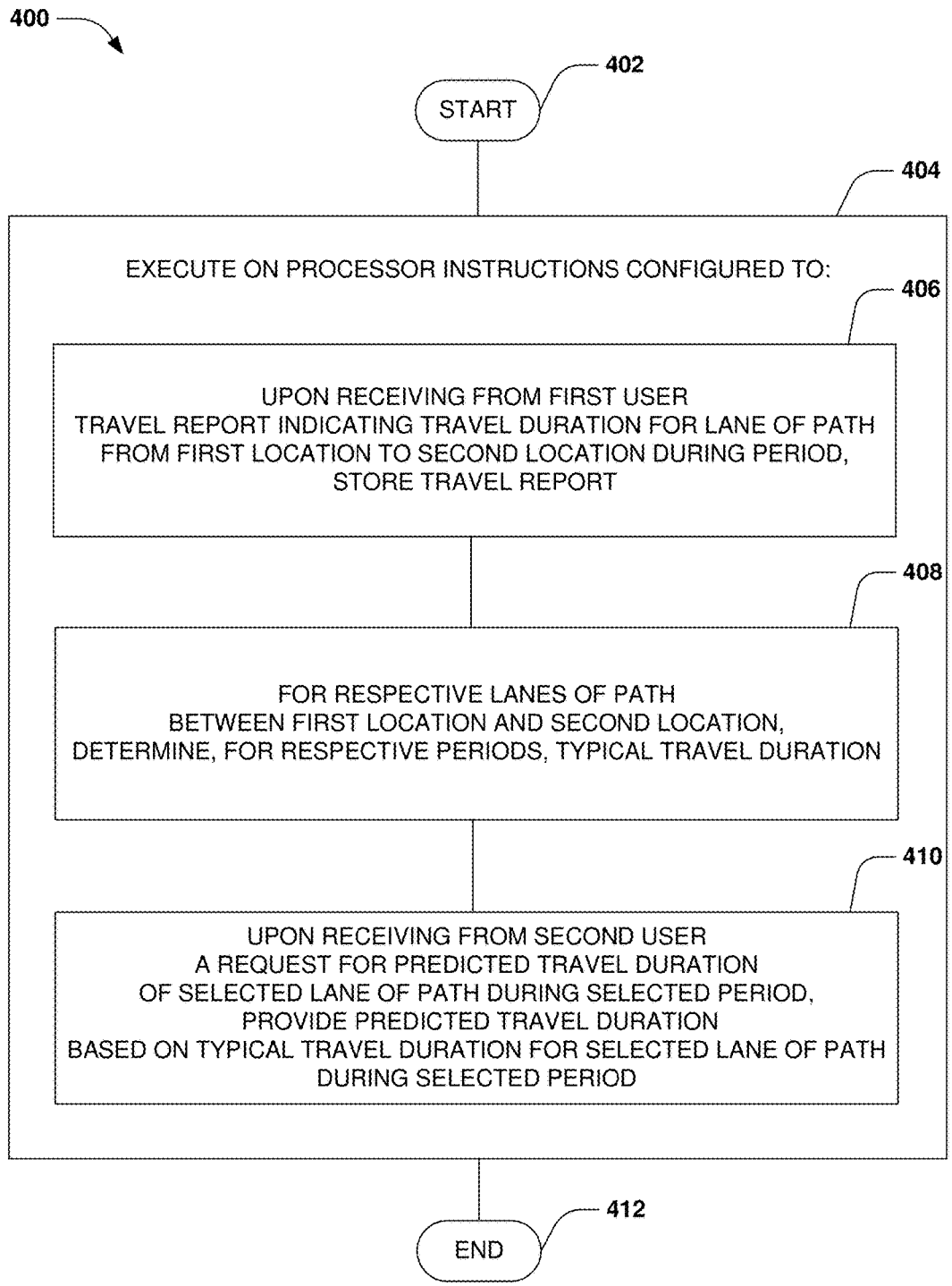
FIG. 4 is an illustration of an example method of providing a travel service to users who are traveling on a path comprising at least two lanes, in accordance with the techniques presented herein.

FIG. 4 presents a first example embodiment of the techniques presented herein, illustrated as an example method 400 of providing a travel service 208 to users 102 of vehicles 104 operating on a path 106. The example method 300 may be implemented on a server having a processor, and that is in communication with devices of users 102 operating within vehicles 104. The example method 300 may be implemented, e.g., as a set of instructions stored in a memory component of the server (e.g., a memory circuit, a platter of a hard disk drive, a solid-state memory component, or a magnetic or optical disc) that, when executed by the processor of the server, cause the server to perform the techniques presented herein.

The example method 400 begins at 402 and involves executing 404 the instructions on the processor. Specifically, the instructions cause the server to, upon receiving from a first user 102 a travel report 210 indicating a travel condition for a lane 112 of a path 106 between a first location 108 and a second location 110 during a period, store 406 the travel report 112. The instructions further cause the server to, for the respective lanes 112 of the path 106 between the first location 108 and the second location 110, determine 408, for the respective periods, a typical travel duration for the lane 112 according to the travel conditions during the period. The instructions further cause the server to, upon receiving from a second user 102 a request for a predicted travel duration of a selected lane 218 of the path 106 during a selected period, provide 410 a predicted travel duration based on the typical travel duration for the selected lane 218 of the path 106 during the selected period. In this manner, the server advises the second user 102 of the travel duration of the selected path 218 based upon the lane conditions reported by the first user 102 in accordance with the techniques presented herein, and so ends at 410.

Figure 5:
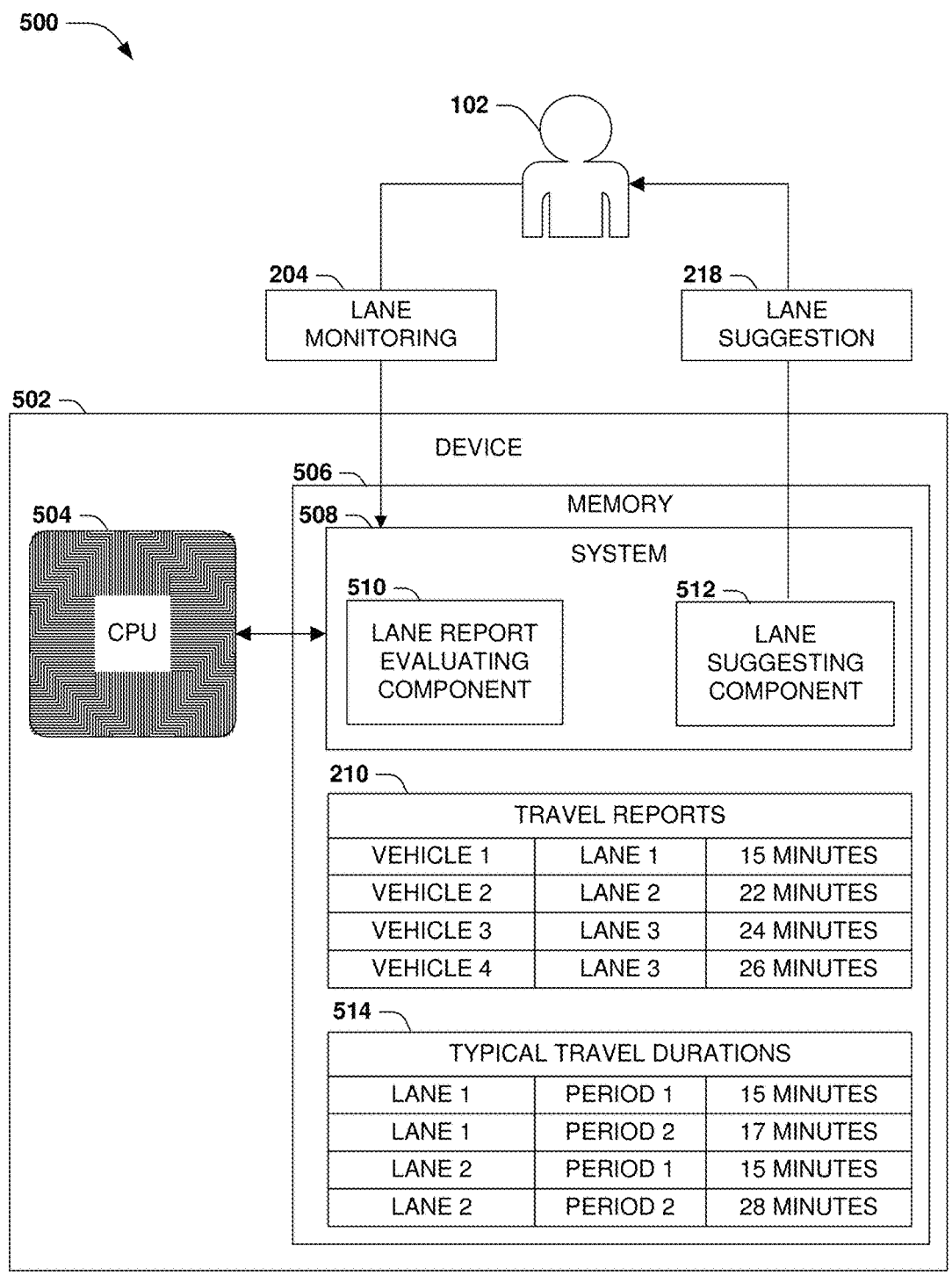
FIG. 5 is an illustration of an example device that advises a user of a selected lane, among at least two lanes of a path between a first location and a second location, in accordance with the techniques presented herein.

FIG. 5 presents an illustration of an example scenario 500 featuring a third example embodiment of the techniques presented herein, illustrated as an example system 508 for advising a user 110 to choose among the lanes 112 of a path 106 that the user is traveling between a first location 108 and a second location 110. The example system 508 may be implemented, e.g., on a device 502 having a processor 504 and a memory 506. Such device 502 may be operating within the vehicle 104 of the user 102, and/or may operate as part of a travel service provided to the user 102 by a server. Respective components of the example system 508 may be implemented, e.g., as a set of instructions stored in a memory 506 of the device 502 and executable on the processor 504 of the device 502, such that the interoperation of the components causes the device 502 to operate according to the techniques presented herein.

The example system 508 comprises a lane report evaluation component 510 that receives and/or determines a travel report 210 indicating a lane condition of a lane 112 of the path 106 based upon lane monitoring 204 gathered during an operation of a vehicle 104 on the path 106. The travel report 210 may be received from the user 102, the vehicle 104, and/or another user 102 of another vehicle 104, and may be reported and/or received from a travel service 208. As one such example, the travel reports 210 may be utilized to determine typical travel durations 514 of the respective lanes 112 of the path 106 during typical periods (e.g., a typical travel duration 514 of a left lane 112 and a right lane 112 of the path both during a morning commute period, and during a weekend evening period). The example system 508 also comprises a lane suggesting component 512 that presents the lane suggestion to the user 102, e.g., by advising the user 102 to choose the selected lane 218 while traveling on the path 106 from the first location 108 to the second location 110. In this manner, the example system 508 may enable the sample device 502 to advise the user 102 in the operation of the vehicle 104 based on the lane conditions of the respective lanes in accordance with the techniques presented herein.

Still another embodiment involves a computer-readable medium comprising processor-executable instructions configured to apply the techniques presented herein. Such computer-readable media may include, e.g., computer-readable storage media involving a tangible device, such as a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a CD-R, DVD-R, or floppy disc), encoding a set of computer-readable instructions that, when executed by a processor of a device, cause the device to implement the techniques presented herein. Such computer-readable media may also include (as a class of technologies that are distinct from computer-readable storage media) various types of communications media, such as a signal that may be propagated through various physical phenomena (e.g., an electromagnetic signal, a sound wave signal, or an optical signal) and in various wired scenarios (e.g., via an Ethernet or fiber optic cable) and/or wireless scenarios (e.g., a wireless local area network (WLAN) such as WiFi, a personal area network (PAN) such as Bluetooth, or a cellular or radio network), and which encodes a set of computer-readable instructions that, when executed by a processor of a device, cause the device to implement the techniques presented herein.

Figure 6:
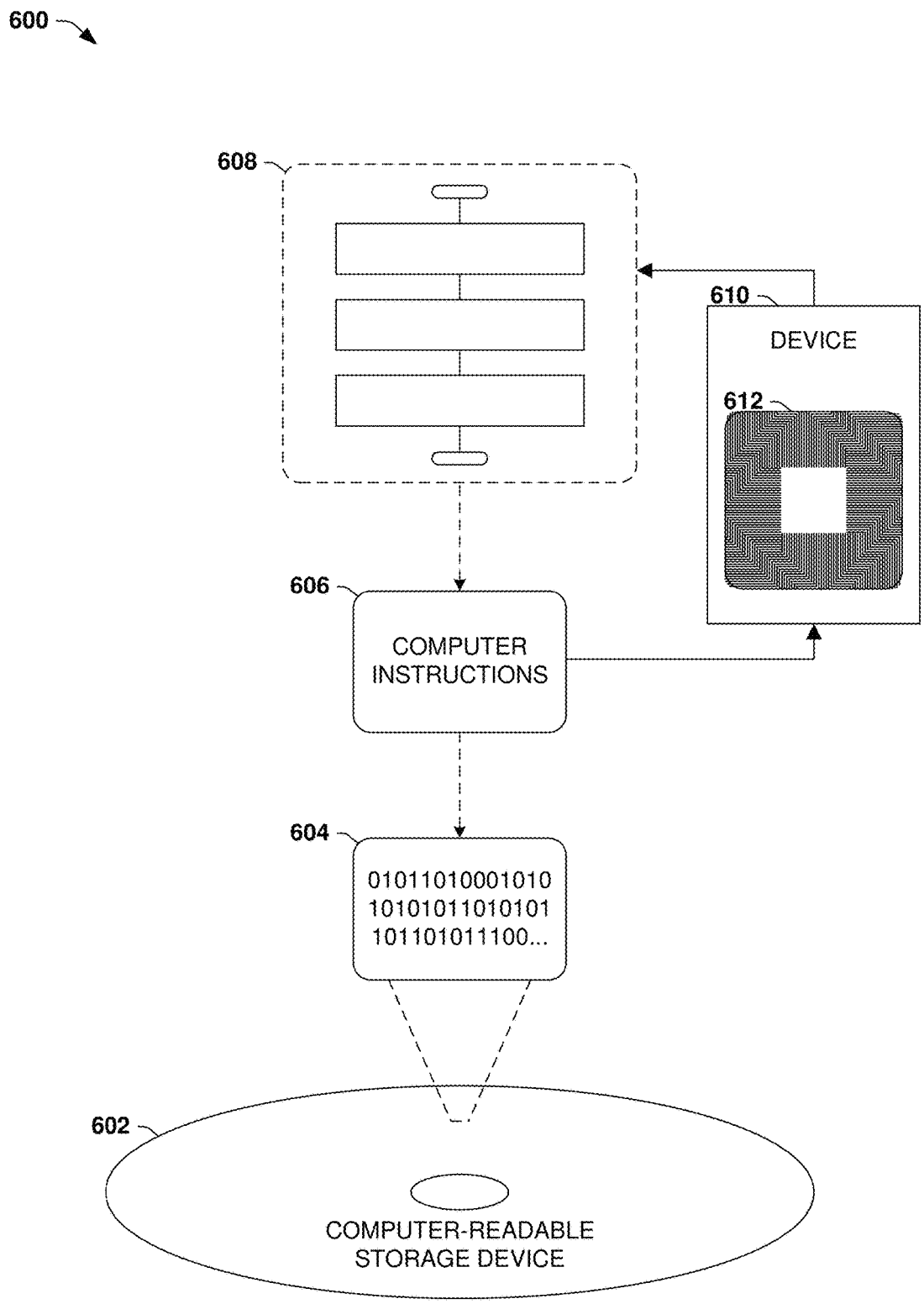
FIG. 6 is an illustration of an example computer-readable medium comprising processor-executable instructions configured to embody one or more of the provisions set forth herein.

An example computer-readable medium that may be devised in these ways is illustrated in FIG. 6, wherein the implementation 600 comprises a computer-readable medium 602 (e.g., a CD-R, DVD-R, or a platter of a hard disk drive), on which is encoded computer-readable data 604. This computer-readable data 604 in turn comprises a set of computer instructions 606 configured to operate according to the principles set forth herein. Many such computer-readable media may be devised by those of ordinary skill in the art that are configured to operate in accordance with the techniques presented herein.

E. Variable Aspects

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in various embodiments (e.g., the example method 300 of FIG. 3; the example method 400 of FIG. 4; the example system 508 of FIG. 5; and the example computer-readable storage device 602 of FIG. 6) to confer individual and/or synergistic advantages upon such embodiments.

E1. Scenarios

A first aspect that may vary among embodiments of these techniques relates to the scenarios wherein such techniques may be utilized.

As a first example of this first aspect, the techniques presented herein may be used with many types of vehicles 104, including automobiles, motorcycles, trucks, trains, buses, watercraft, aircraft, drones, and spacecraft. The techniques may also be utilized to advise the user 102 while traveling along many types of paths 106, such as a roadway, highway, sidewalk, dirt or grass path, waterway, and airspace. Such vehicles may be controlled by one or more humans, may be autonomous, or may involve a combination thereof, such as an autonomous automobile that can also be controlled by a human. Moreover, such paths 106 may be divided into lanes 112 in a variety of ways, such as a conceptual partitioning of the path 106 into lanes 112 and/or a demarcation of the lanes 112 through visual and/or electronic identifiers.

As a second example of this first aspect, the techniques presented herein may utilize a variety of sources of information to detect the conditions of the lanes 112 of the path 106. As a first example, when requested to maintain a selected speed, the device may utilize acceleration and braking rates that are typical of the user 102 (e.g., accelerating and braking aggressively when an aggressive driver is operating the vehicle 104, and accelerating and braking more gradually when a relaxed driver is operating the vehicle 104). As a second example, while the user 110 is controlling the speed of the vehicle 104, the device may compare the speed of the vehicle 104 with the posted speed limit in order to determine the user's typical preference for driving over, at, or under the speed limit; and when requested to maintain a steady speed, the device may continuously adapt the target speed with respect to the current speed limit in order to reflect the speed preferences of the user 102. Other examples of the types of driving behaviors that may indicate the lane condition of the lane 112 of the path 106 include the braking rates of the user 102 (e.g., whether the user prefers stopping over short distances or more gradually over longer distances); the speed and/or turning profile of the vehicle 104 while traversing curves; the altitude and/or attitude of an airborne vehicle 104; a maintained distance of the vehicle 104 with respect to at least one other vehicle 104; the preference of the user 102 to yield to other vehicles 104; and a lane change frequency of the vehicle 104 between at least two lanes 112. Alternatively or additionally, such techniques may utilize a variety of other information to detect the lane conditions of the lanes 112 of the path 106, including the time of day; sunny, overcast, foggy, rainy, snowing, and/or freezing weather conditions; a vehicle causeway type context (e.g., an unpaved local road, a residential side street, a main roadway, or a highway); a traffic congestion context (e.g., the volume of traffic in the vicinity of the vehicle 104); a vehicle speed of at least one other vehicle 104 operating near the vehicle 104 (e.g., if the vehicle 104 is passing, being passed by, or keeping pace with other vehicles 104); the route of the vehicle 104 (e.g., a short local route, a longer cross-city route, or a long-distance route between cities); and a vehicle condition context (e.g., the maintenance condition and/or cargo contents of the vehicle 104); and a vehicle passenger context (e.g., the number and identities of other passengers aboard the vehicle 104).

As a third example of this first aspect, the techniques presented herein may utilize a variety of sources of information to choose a selected lane 218 for recommendation to the user 102, in addition to the predicted travel duration of the lane 112 while traveling the path 106 between the first location 108 and the second location 110. Such information may include, e.g., a lane preference of the user 102 (e.g., whether the user 102 prefers to operate the vehicle 104 in a particular lane); sensitivities of the user 102 to conditions such as traffic density, speed, speed fluctuation, lane change frequency, costs, and ecological impact; and driving behaviors of the user 102 (e.g., a preferred amount of advance notice before the user 102 is compelled to change lanes 112 in order to adhere to a selected route). These and other variations may arise regarding the scenarios within which the techniques may be advantageously utilized.

E2. Lane and Lane Condition Determination

A second aspect that may vary among embodiments of these techniques involves the determination of the lane 112 of a user 102, as well as the lane condition of the lane 112 and, optionally, other lanes 112 of the path 106 that are detectable by a device of the user 102. The determination of the lane 112 of the user 102 may be utilized, e.g., to determine which lane 112 the user 102 has occupied or is occupying to travel the path 106 from the first location 108 to the second location 110, and/or the lane 112 of the path 106 that is described by a travel report 210 received by the travel service 208.

Figure 7:
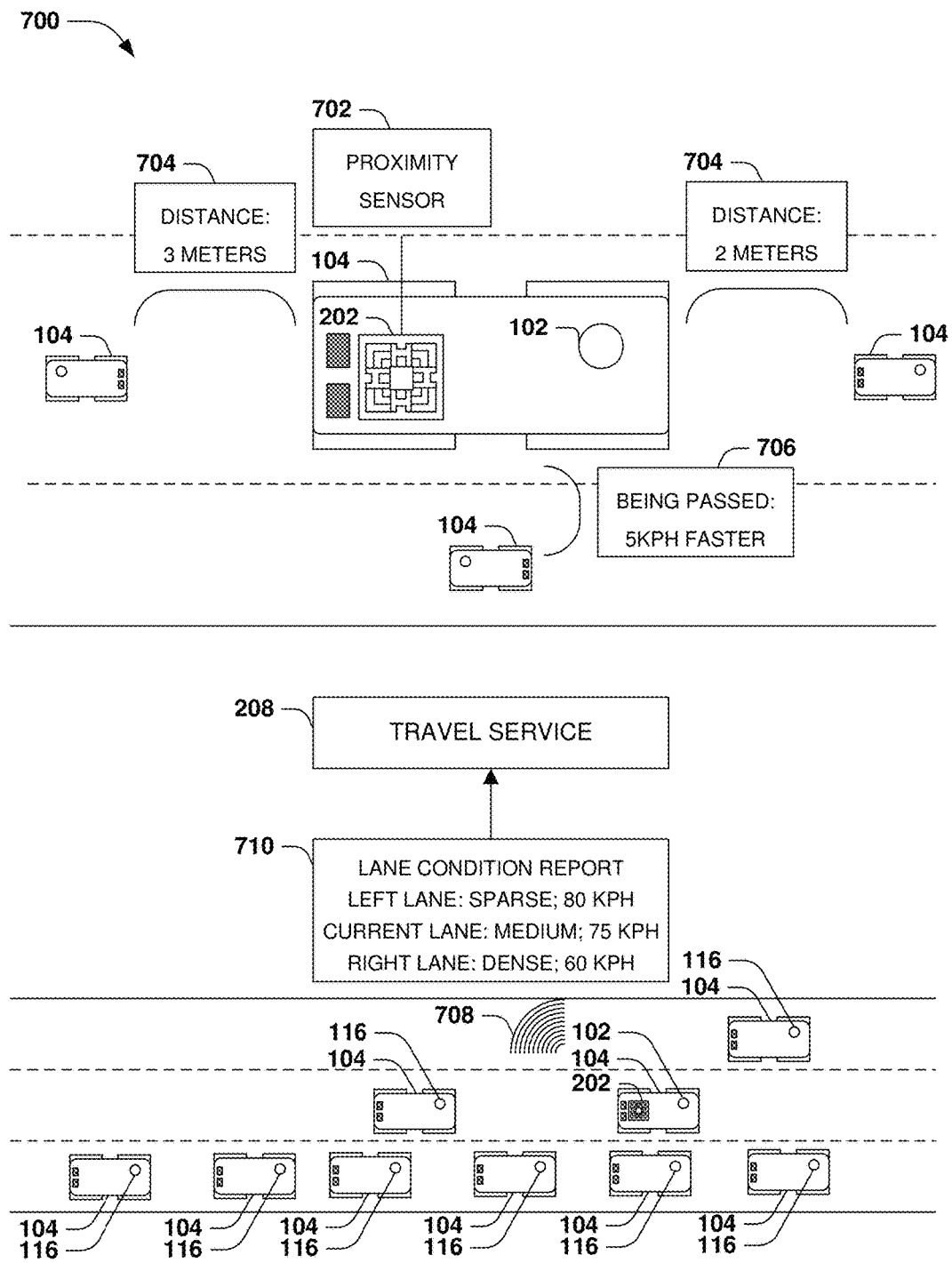
FIG. 7 is an illustration of a first example technique for monitoring lane conditions of the lanes of a path, in accordance with the techniques presented herein.

FIG. 7 presents an illustration of an example scenario 700 featuring a first variation of this second aspect, wherein the lane 112 of the path 106 occupied by a vehicle 104 of the user 102 is detected according to a proximity sensor 702 of the vehicle 104 that includes a variety of techniques, such as visual evaluation of camera data; ranging data gathered by sonar, radar, and/or lidar detection; and/or electronic communication with other vehicles 104 operating on the path 106. In this example scenario 700, the vehicle 104 is equipped with a proximity sensor 702 that detects a proximity of the vehicle 104 with respect to other vehicles 104 operating on the path 106, such as a distance 704 between the vehicle 104 and another vehicle 104 that is ahead of and/or behind the vehicle 104 of the user 102; the relative speeds of the vehicles 104 ahead of and/or behind the user 102; and/or the rates of acceleration, braking, turning, and/or swerving by the user 102 and the drivers 116 of the other vehicles 104. The proximity sensor 702 may also detect information about vehicles 104 in other lanes 112 of the path 106, such as the relative or absolute speeds of vehicles 104 in adjacent lanes 112, and/or whether or not such vehicles 104 are passing 706 and/or are being passed by the vehicle 104. The device 202 may transmit 708 the information detected by the proximity sensor 702 to a travel service 208, e.g., as a lane condition report 710 indicating the conditions of the respective lanes 112 of the path 106, optionally including information about other (e.g., adjacent) lanes of the path 112 and/or vehicles 104 utilizing such lanes 112, and/or information about the user 102 and/or the travel along the path 106, such as the travel duration between the first location 108 and the second location 110.

Figure 8:
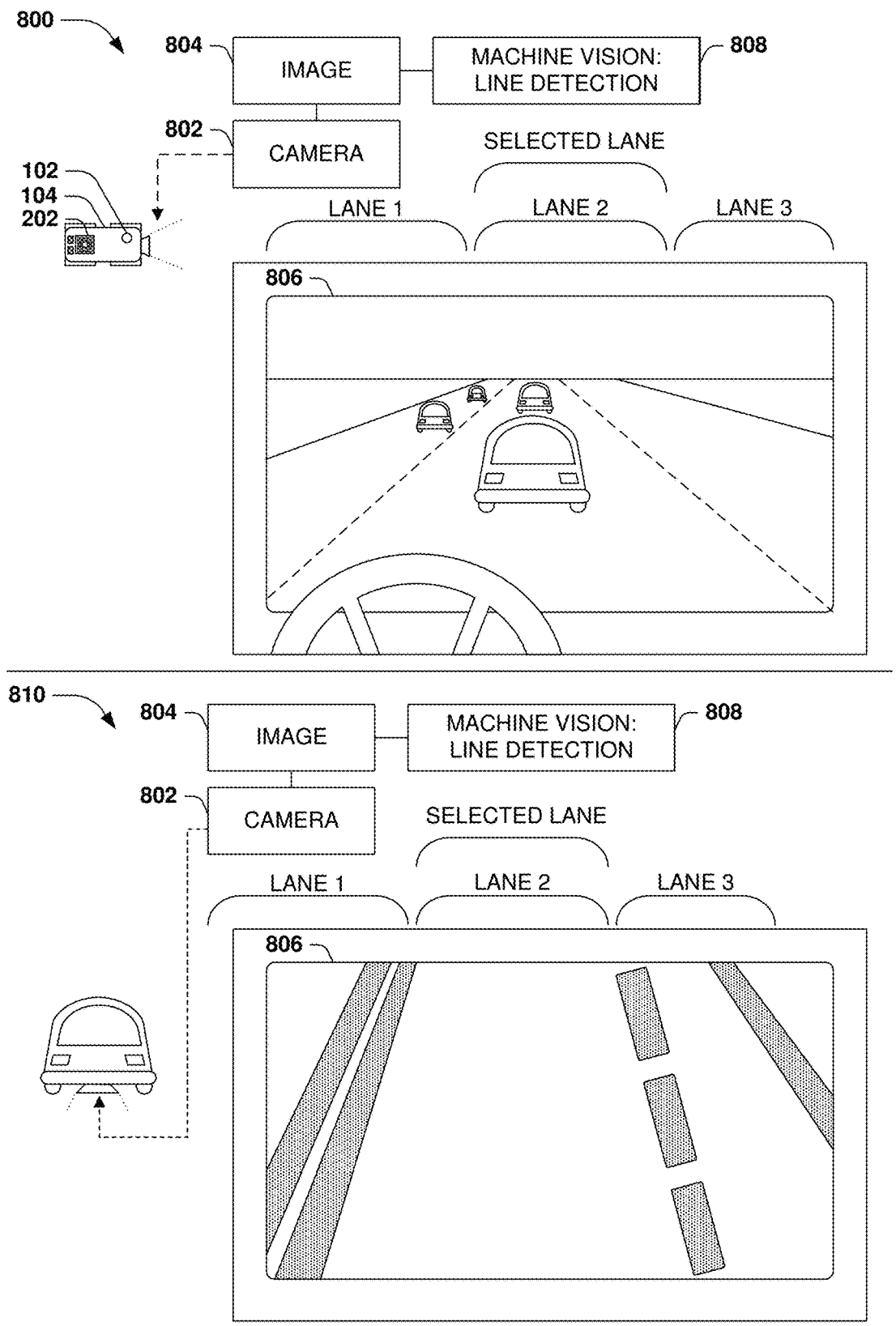
FIG. 8 is an illustration of a second example technique for monitoring lane conditions of the lanes of a path, in accordance with the techniques presented herein.

FIG. 8 presents an illustration of example scenarios featuring a second set of variations of this second aspect, wherein the lanes 112 and/or lane conditions 710 of the respective lanes 112 of the path 106 are determined by a machine vision technique 808. As a first example scenario 802, a device 202 on board the vehicle 104 may include and/or be in communication with a forward-mounted camera 802 that captures a forward-facing image 804 (e.g., through a windshield 806 of the vehicle 104). A machine vision technique 808 may be applied to the image 804, such as a line detection algorithm that is configured to detect visible lines indicating the respective lanes 112 of the path 106. The position of the vehicle 104 on the path 106 may also be extrapolated by the machine vision technique 808, and may therefore be utilized to determine the selected lane that is currently occupied by the vehicle 104. Alternatively or additionally, other machine vision techniques may be applied to the image 804 to detect the lane conditions 710 of the lanes 112 of the path 106, such as object recognition to detect and optionally count a number of visible vehicles 104 ahead of the vehicle 104 of the user 102 in the respective lanes 112, and/or visual sizing machine vision techniques that estimate a distance of vehicles 104 ahead of the vehicle 104 of the user 102. As a second example scenario 810, a downward-facing camera 802 may capture a downward-facing image 804 of the path 106, and a line detection machine vision technique 808 may be utilized to detect the visible lines indicating the lanes 112 of the path 106, and/or the selected lane that is currently occupied by the vehicle 104 of the user 102.

E3. Evaluation of Lane Travel Duration

A third aspect that may vary among embodiments of the techniques presented herein involves the evaluation of the travel duration of the respective lanes 112 of the path 106.

As a first variation of this third aspect, the periods through which a travel service 208 evaluates the travel durations of the lanes 112 of the path 106 may be selected in a variety of ways. As a first such example, the periods may be selected according to a predefined duration (e.g., one-hour or fifteen-minute blocks). As a second such example, the periods may be selected to reflect different conditions of the lanes 112 and/or path 106 (e.g., a first period selected to represent a morning commute period; a second period selected to represent a midday period; a third period selected to represent an evening commute period; and a fourth period selected to represent a weekend period). As a third such example, the periods may be selected to reflect different conditions of an environment of the path 106 (e.g., a first period selected as a period of rainy weather, and a second period selected as a period of dry weather). As a fourth such example, the periods may be identified by correlating the travel reports 210 of the vehicles 104, e.g., by detecting that a cluster of vehicles 104 traveling within a certain range of time may reflect consistently similar travel durations).

As a second variation of this third aspect, a travel report 210 provided by a device 204 of a vehicle 104 may report a speed of the first user 102 while traveling a selected lane 112 of the path 106 between the first location 108 and the second location 110. A travel service 208 may therefore determine a typical travel duration of the respective lanes 112 of the path 106 based on the collection of such travel reports 210 according to the speeds of the users 102 traveling the lane 112 of the path 106 between the first location 108 and the second location 110 during the period (e.g., a typical travel duration for users 102 traveling in the left lane 112 of the path 106 during a morning commute period). For example, among the travel durations of the users 102 traveling the lane 112 of the path 106 during the period, the travel service 208 may determine the typical travel duration according to an average travel duration (e.g., an arithmetic mean, median, and/or mode travel duration) of the travel durations reported by the users 102, or according to a shortest and/or longest travel duration among the users 102 traveling the lane 112 of the path 106 during the period.

As a third variation of this third aspect, a travel service 208 may be configured to correlate, for the respective lanes 112 of the path 106, the travel durations reported for the lane 112 according to a lane condition of the selected lane 112 of the path 106. As a first such example, a particular lane 112 of the path 106 may be prone to frost, ice, or slippery conditions, and may therefore exhibit markedly different travel durations during a particular period (e.g., during a morning commute period) on days that are wet and/or cold than on days that are not. As a second such example, a particular lane 112 of the path 106 may be the focus of sporadic construction, and may therefore exhibit markedly different travel durations when construction is and is not under way. The travel service 208 may be configured to correlate the travel reports 210 with respective lane conditions, and may utilize such lane conditions to provide a more accurate estimation of typical travel durations of the lane 112 of the path 106, which may in turn enable a more accurate predicted travel duration for the lane 112 on behalf of a user 102 of a vehicle 104.

As a fourth variation of this third aspect, a device 202 of the user 102 and/or vehicle 104 may also participate in the collection of information by the travel service 208. For example, the device 202 may submit to the travel service 208 a travel report 210 that further specifies the selected lane 218 that was chosen by the user 102 while traveling the path 106 between the first location 108 and the second location 110, and/or the travel duration experienced by the user 102 while traveling the path 106 from the first location 108 to the second location 110.

As a fifth variation of this third aspect, the device 202 and/or travel service 208 may utilize a variety of techniques to perform the identification of the selected lane 218 based on such information on behalf of a particular user 102. As a first such example, a travel report 210 received from a first user 102 may specify at least one intermediate location of the user 102 while traveling the path 106 between the first location 108 and the second location 110, and the device 202 and/or travel service 208 may determine, from the at least one intermediate location, the lane 112 of the path 106 of the user 102 while traveling the path 106 between the first location 108 and the second location 108. As one such example, for the respective users 102 of a first user set who are traveling or have traveled the path 106 between the first location 108 and the second location 110, a travel duration of the user 102 may be determined. A histogram may be generated of the travel durations of the users 102 of the first user set, and an arithmetic mean of the travel durations of the histogram may be identified. Travel duration may be identified according to the arithmetic mean for the lane 112 of the path 106 between the first location 108 and the second location 110.

Figure 9:
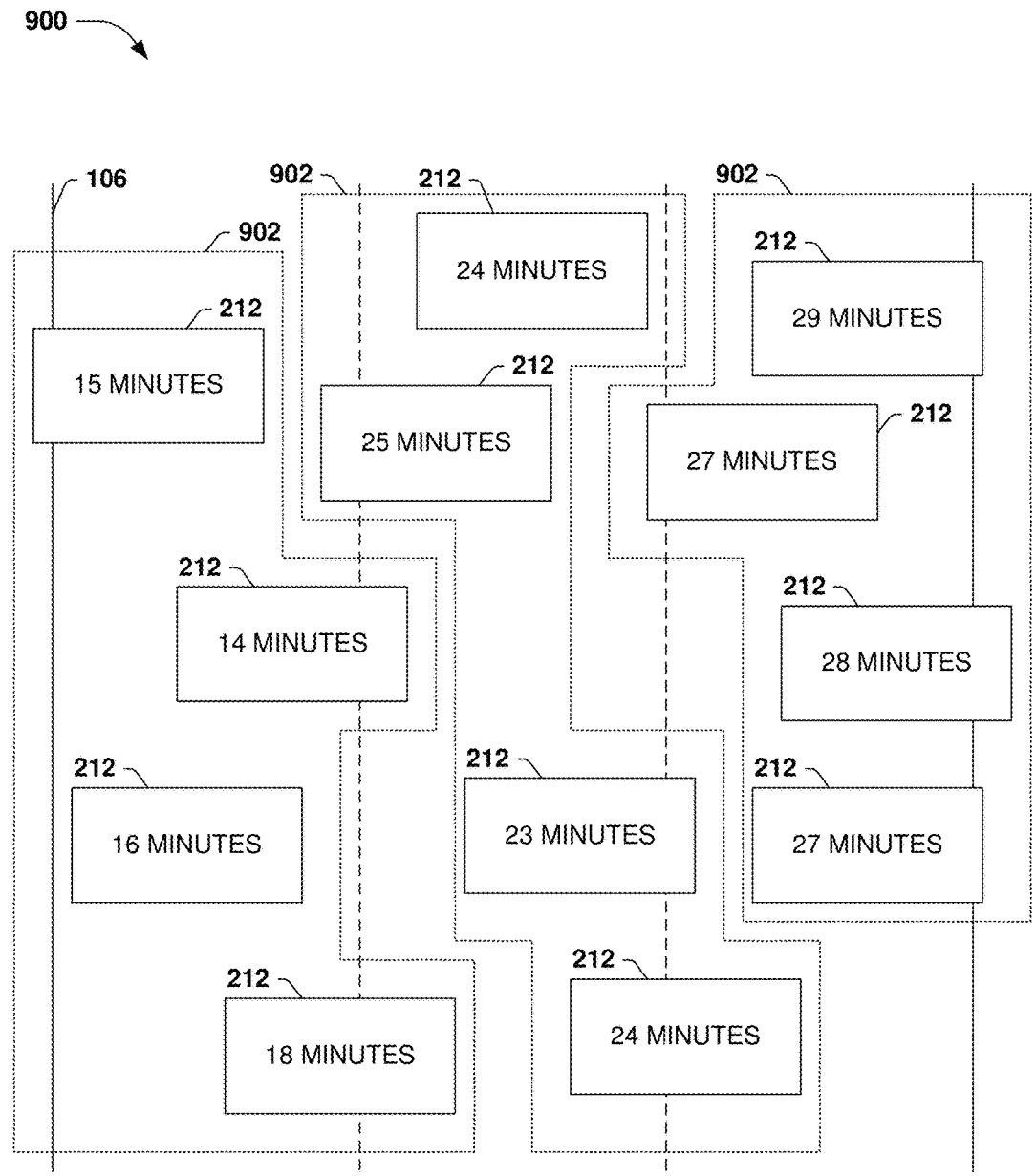
FIG. 9 is an illustration of an example technique for evaluating a set of lane condition reports provided by a set of users with respect to the lanes of a path, in accordance with the techniques presented herein.

FIG. 9 presents an illustration of an example scenario 900 wherein respective users 102 are clustered to determine the lanes 112 of the path 106 that are associated with the respective travel reports 212 submitted by various users. In this example scenario 900, the devices 202 of the respective users 102 submit travel reports 212 indicating the travel duration of the users 102 while traveling the path 106 from the first location 108 to the second location 110. In many such scenarios, the location detection may not be suitably precise to determine which lane 112 the respective users 102 have or had selected; e.g., inaccuracies in location information, calibration, and/or mapping data may suggest that users 102 whose vehicles 104 are occupying a particular lane 112 are or were, instead, between lanes 112 and/or in an adjacent lane 112. Accordingly, a clustering technique may be utilized to correlate travel reports 212 that are within a particular range of locations, and that also indicate a particularly consistent set of travel durations. For example, a first cluster 902 of travel reports 212 may exhibit a broader set of locations that exceed the physical width of the lane 112, but may also be correlated by travel duration, and may therefore be distinguished from travel reports 212 of a second cluster 902 that overlap the locations of the first cluster 902 but that exhibit a markedly different correlation of travel durations. In this manner, incomplete information about lane selection by users 102 and travel reports 212 may be supplemented with other information to yield a determination of the typical travel durations of the lanes 112.

Figure 10:
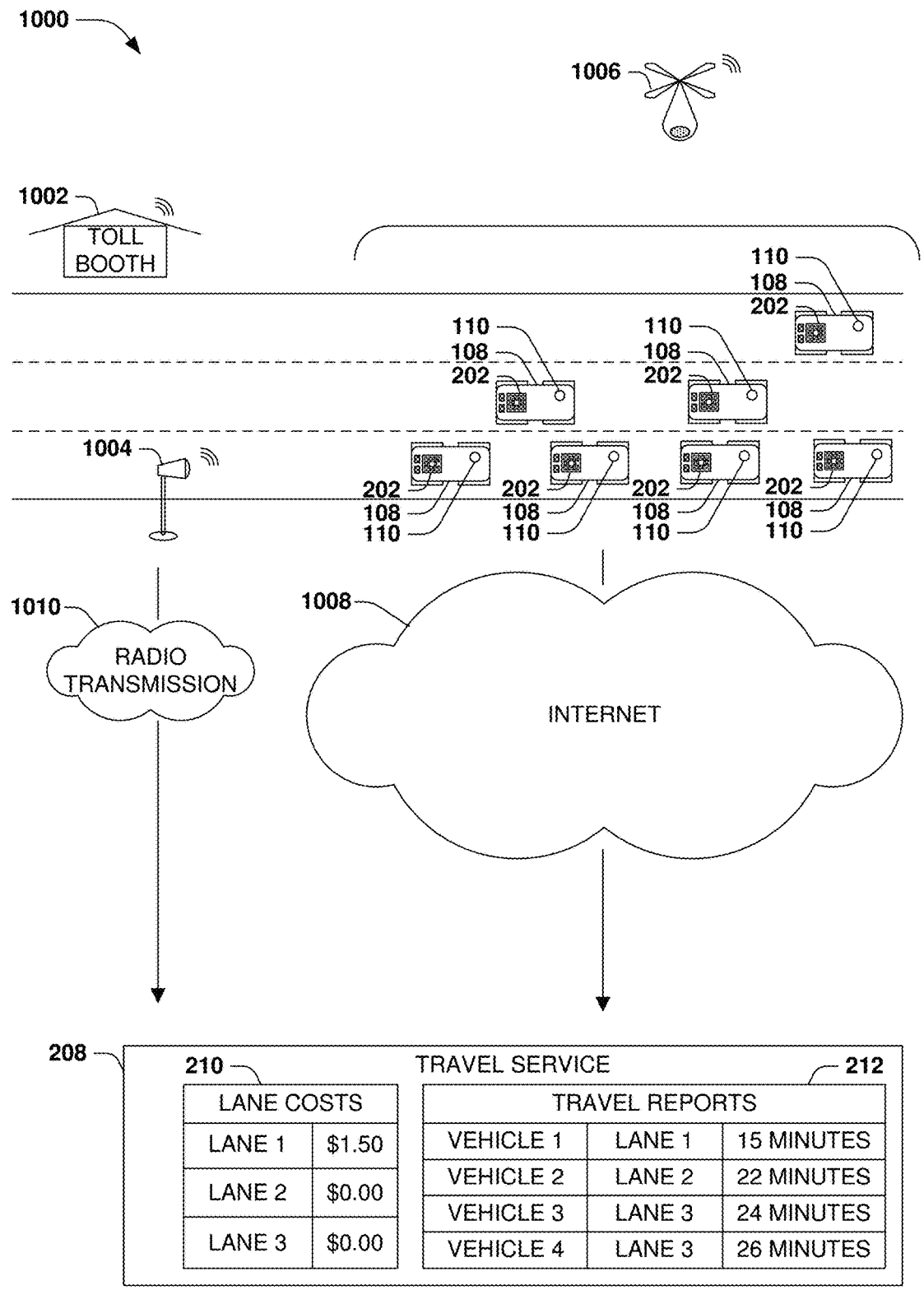
FIG. 10 is an illustration of an example technique for delivering lane condition reports from various sources to a travel service, in accordance with the techniques presented herein.

FIG. 10 is an illustration of an example scenario 1000 featuring a collection of travel reports 212 about the lanes 112 of a path 106. In this example scenario 1000, a set of vehicles 108 is operated by a set of users 102 on a path 106, and information about the lanes 112 of the path 106 may be collected by a travel service 208 as a set of travel reports 212, including such information as the vehicles 108 in each lane 112; the travel duration of each vehicle 108 in each lane 112; and other information, such as lane costs 210 during the observed period. Such travel reports 212 may be collected from devices 202 on board the vehicles 108; from the users 102 of such vehicles 108; from toll booths 1002, traffic cameras 1004, or other forms of path monitoring; and/or from aerial surveillance, such as from a drone 1006. The travel reports 212 may be transmitted to the travel service 208 in a variety of ways, including the internet 1008 and radio transmissions 1010, and may be stored by the travel service 208 to facilitate the evaluation of information about the respective lanes 112 of the path 106, including the typical travel durations for the respective lanes 112 of the path 106. Many such techniques may be utilized to determine the typical travel durations for the respective lanes 112 of the path 106 during respective periods in accordance with the techniques presented herein.

E4. Lane Selection

A fourth aspect that may vary among embodiments of the techniques presented herein involves the manner of determining, among the lanes 112 of the path 106, a selected lane 218 to be recommended to the user 102.

As a first variation of this fourth aspect, the determination of a selected lane 218 may be performed by the device 202 of the user 102; e.g., the travel service 208 may collect travel reports 212 and send them to the device 202, and/or typical travel durations determined for the respective lanes 112, to be further evaluated by the device 202. Alternatively or additionally, the travel service 208 may identify the selected lane 218 to be recommended to the user 104, and may transmit the identification of the selected lane 218 to the device 202.

As a second variation of this fourth aspect, the identification of the selected lane 218 may be based upon a variety of information in addition to the predicted travel durations of the respective lanes 112. Such evaluation may lead to the selection of a first lane 112 over a second lane 112 having a lower predicted travel duration if the other information that is also evaluated mitigates in favor of the first lane 112.

As a first example of this second variation of this fourth aspect, at least one lane 112 may be associated with a lane cost 210 that is assessed to users 102 traveling in the lane 112, and identifying the selected lane 218 may include a comparison of the predicted travel durations of the lanes 112 of the path 106 with the lane costs 210 of the lanes 112. Such lane costs 210 may be statically defined for the respective lanes 112 (e.g., a particular lane 112 may always be associated with a constant lane cost 210); may vary at different times of day; and/or may be controlled according to various conditions, such that the travel service 208 may further detect a current lane cost of the lane 112 for use in the comparison. The cost comparison may also include an evaluation of the comparative advantage of the lane 112 in terms of reduced travel duration (e.g., whether the reduction in travel duration from using the lane 112 substantiates the lane cost 210 as compared with another lane 112), and/or a cost sensitivity of the user 102 (e.g., the user 102 may specify a cost budget and/or advantage ratio, such as undertaking a certain lane cost 210 only if the reduction in travel duration exceeds a particular threshold travel duration reduction). In one such embodiment, a driving behavior of the user 102 may be monitored to detect at least one lane selection by the user 102 of a lane 112 having a lane cost 210 (e.g., an "opt-in" selection of the lane 112 by the user 102), and the further identification of selected lanes 218 may be based upon an extrapolation of the cost sensitivity of the user 102 that is inferred from the user's driving behavior. For example, the device 202 may provide a presentation of the selected lane 108 that includes the lane cost of a first lane 112 and a predicted travel lane duration reduction as compared with a second lane 112, and the cost sensitivity of the user 102 may be determined according to the lane selection of the user 102 in response to the presentation.

As a second example of this second variation of this fourth aspect, various lanes 112 of the path 106 may be associated with a lane restriction, such as a minimum occupancy of a high-occupancy vehicle (HOV) lane; a time restriction during which the lane 112 may be traveled; a maximum and/or minimum speed that may be utilized by vehicles 104 traveling in the lane 112; and/or a vehicle class of vehicles 104 that are permitted in and/or restricted from the lane 112 (e.g., a height, weight, and/or wheel maximum). While identifying the selected lane 218 to recommend to the user 102, the device 202 and/or travel service 208 may determine whether the user 102 and/or vehicle 104 satisfies the lane restrictions of the respective lanes 112, and may identify a lane 112 as the selected lane 218 only if such lane restrictions are satisfied.

As a third example of this second variation of this fourth aspect, the selected lanes 218 among the lanes 112 of the path 106 between the first location 108 and the second location 110 may be determined more broadly according to the route selection of routes by which the user 102 may travel from an origin to a destination. For example, while comparing respective routes from the origin to the destination, the device 202 and/or travel service 208 may also consider the particular lanes 112 of the routes 112, and may identify the selected route 218 to be recommended to the user 102 as part of the identification of a selected route.

Figure 11:
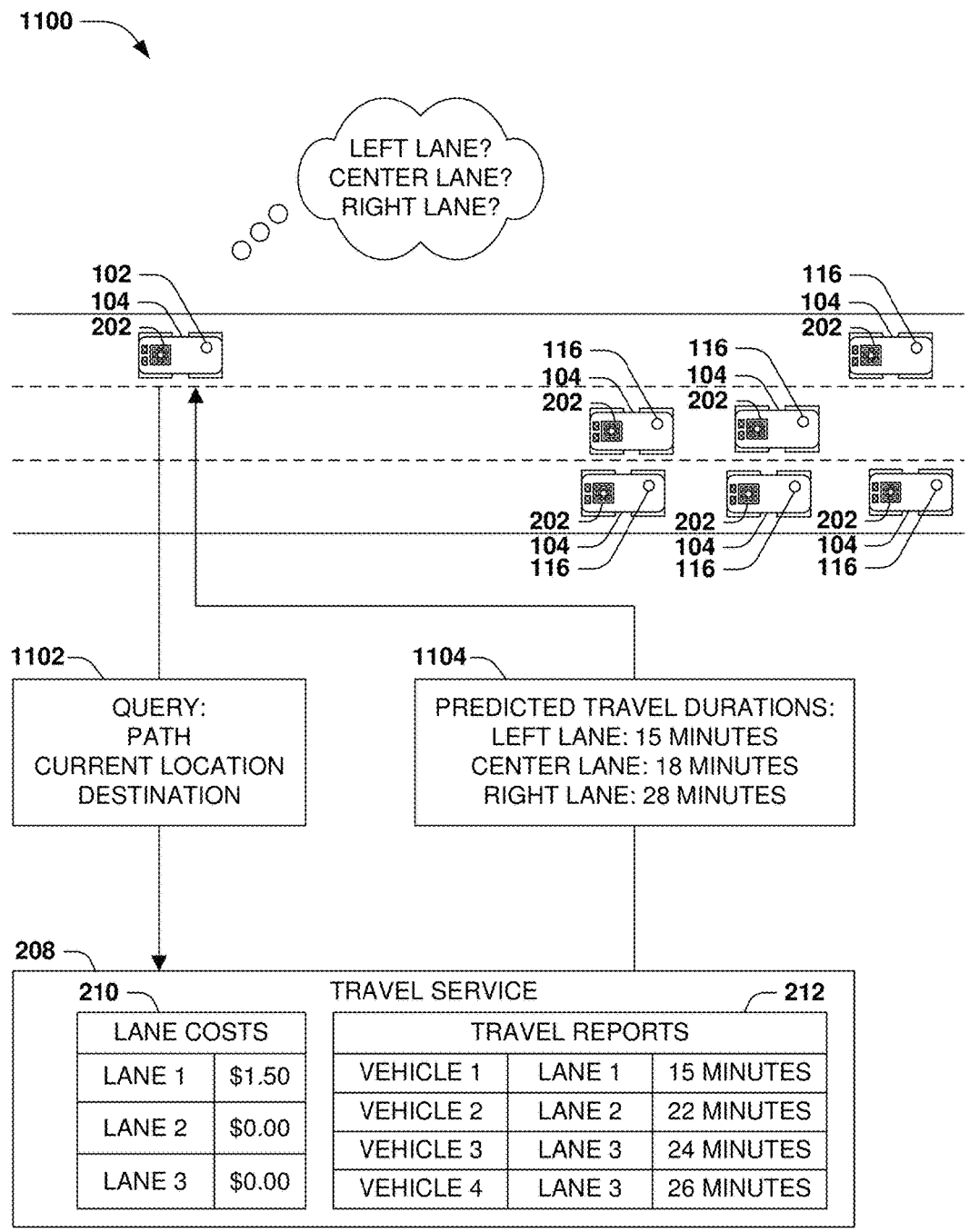
FIG. 11 is an illustration of an example technique for delivering a set of predicted travel times of respective lanes of a path to a user traveling the path between a first location and a second location, in accordance with the techniques presented herein.

FIG. 11 presents an illustration of an example scenario 1100 wherein a user 102 of a vehicle 104 may be advised of a selected lane 218 among a set of lanes 112 of the path 106. As a first such example, the selected lane 218 may be identified based on the predicted travel duration of each lane 112 of the path 106. A device 202 of the user 102 may determine that a lane recommendation may be timely provided to the user 102, and may therefore submit a query 1102 to the travel service 208. The travel service 208 may evaluate the travel reports 212 to determine typical travel durations for the respective lanes 112 of the path 106, and, therefore, a predicted travel duration for each lane 112 of the path 106 that the user 102 of the vehicle 104 may choose. For example, the travel service 208 may be informed, according to current travel reports 212 and/or typically during the current period, that the left lane 112 is sparsely occupied; that the center lane is typically occupied; and that the right lane is heavily occupied. The travel service 208 may therefore transmit to the device 202 a set of predicted travel durations 1104, and, optionally, other information that may be relevant to the identification of the selected lane 218, such as the current lane costs 210 of the respective lanes 112. Using such information, the travel service 208 and/or device 202 on board the vehicle 104 may identify the selected lane 218 for presentation to the user 102. In this manner, the travel service 208 and device 202 on board the vehicle 104 may interoperate to determine the selected lane 218 to be recommended to the user 102 in accordance with the techniques presented herein.

E5. User Advising of Selected Lanes

A fifth aspect that may vary among embodiments of the techniques presented herein involves the manner of advising a user 102 of the selected lane 218 of the path 106.

As a first variation of this fifth aspect, the recommendation of a selected lane 218 may be presented to the user 102 in a variety of ways. As a first such example, the selected lane 218 may be described in absolute terms (e.g., "recommendation: choose the left lane"), or in relative terms (e.g., "recommendation: move one lane to the left"). As a second such example, the device 202 may or may not explain the basis of the recommendation, e.g., the comparative advantage of choosing the selected lane 218 over other lanes 112 of the path 106. Moreover, if the selected lane 218 is also the current lane 112 occupied by the vehicle 104, the device 202 may either present the recommendation (e.g., "recommendation: maintain current lane"), or may defer such recommendation until detecting that the user 102 is considering transitioning to a different lane (e.g., upon detecting the user's activation of a turn signal).

Figure 12:
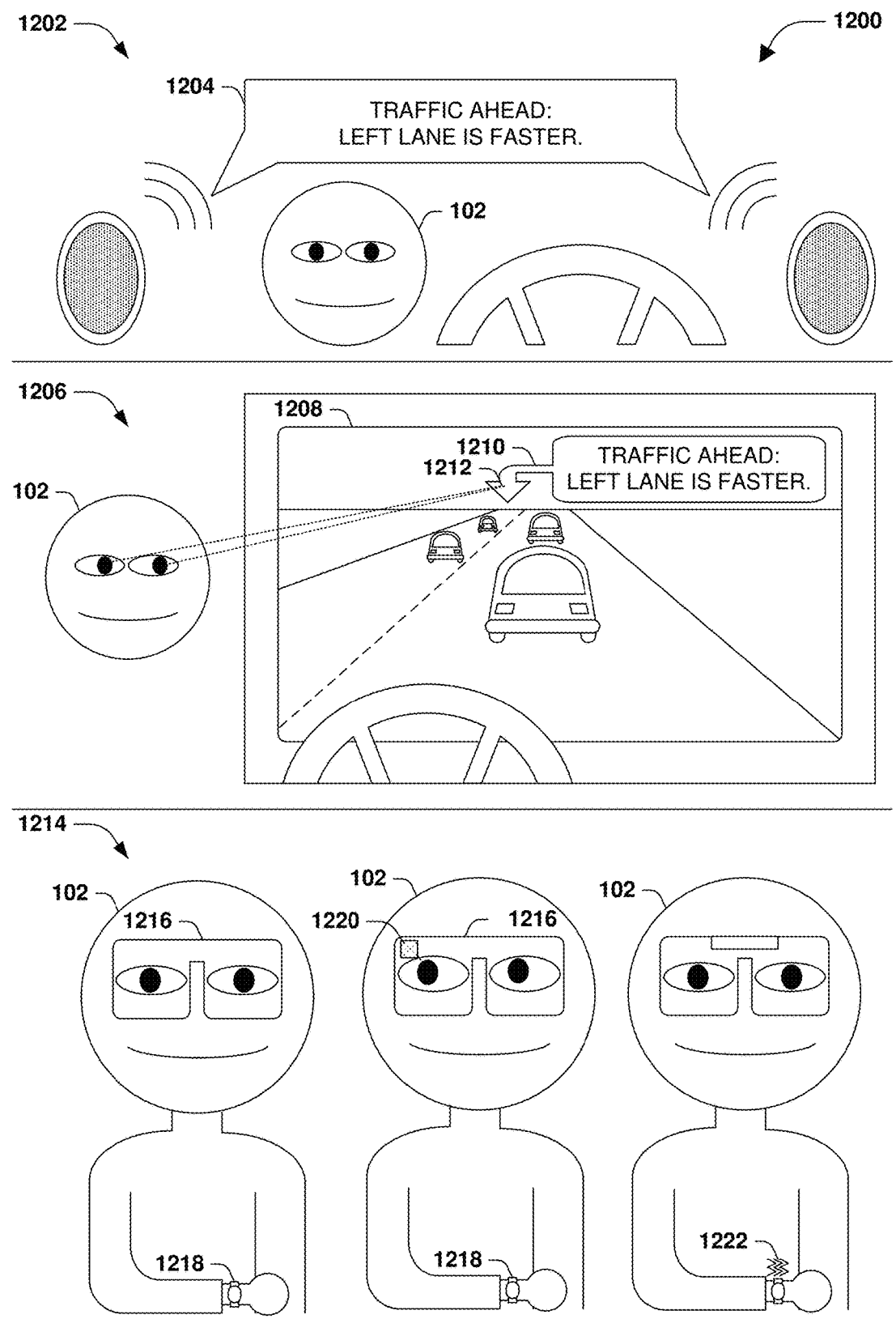
FIG. 12 is an illustration of a set of example techniques for advising a user to choose a selected lane of a path between a first location and a second location, in accordance with the techniques presented herein.

FIG. 12 presents an illustration of a set of exemplary scenarios 1200 whereby the device 202 may advise the user 102 as to the selected lane 218. As a first variation 1202 of this fifth aspect, a visual and/or audial indicator may be presented to the user 102 by the device 202 and/or vehicle 104, such as a light on the dashboard of the vehicle 104 or an audio or voice cue 1204 prompting the user to select a particular lane 112. As a second variation 1206 of this fifth aspect, a visual indicator 1210 may be presented on a window 1208 of the vehicle 104, and, optionally, may be presented at a selected location 1214 on the window 1208 that correlates the visual indicator 1210 with the location 1212 of the selected lane 218 through the window 1208 from the perspective of the user 102 (e.g., presenting a visual arrow and/or highlighting the location of the selected lane 218 when viewed through the window 1208 by the user 102). A third variation 1214 of this fifth aspect, the user 102 may wear one or more wearable devices while operating the vehicle 104, such as a pair of eyeglasses 1216 or a wristwatch 1218. The presentation of the suggestion of the selected lane 218 may be achieved through such wearable devices, e.g., by presenting a visual indicator 1220 within the viewable region of the eyeglasses 1216 worn by the user 102, and/or issuing a vibration alert 1222 through the wristwatch 1218 of the user 1220 to indicate the direction of the selected lane (e.g., flashing a leftward visual indicator 1220 or a vibration alert 1222 on the user's left wrist to indicate a selection of a lane 218 to the left of the user's current lane). Many such techniques may be utilized to recommend the selected lane 218 to the user 102 in accordance with the techniques presented herein.

F. Computing Environment

Figure 13:
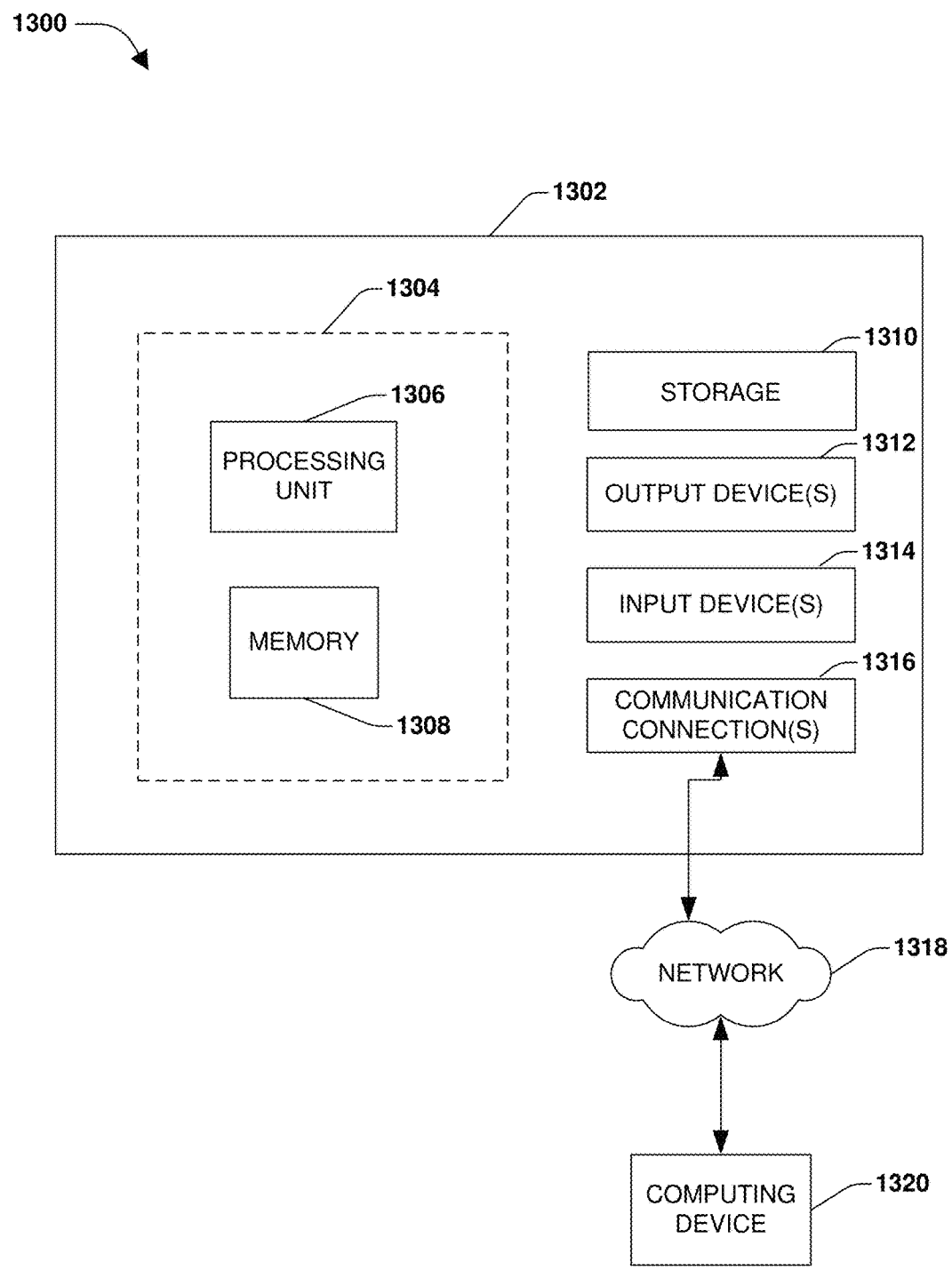
FIG. 13 is an illustration of an example computing environment wherein one or more of the provisions set forth herein may be implemented.

FIG. 13 and the following discussion provide a brief, general description of a suitable computing environment to implement embodiments of one or more of the provisions set forth herein. The operating environment of FIG. 13 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 13 illustrates an example of a system 1300 comprising a computing device 1302 configured to implement one or more embodiments provided herein. In one configuration, computing device 1302 includes at least one processing unit 1306 and memory 1308. Depending on the exact configuration and type of computing device, memory 1308 may be volatile (such as RAM, for example), non-volatile (such as ROM, flash memory, etc., for example) or some combination of the two. This configuration is illustrated in FIG. 13 by dashed line 1304.

In other embodiments, device 1302 may include additional features and/or functionality. For example, device 1302 may also include additional storage (e.g., removable and/or non-removable) including, but not limited to, magnetic storage, optical storage, and the like. Such additional storage is illustrated in FIG. 13 by storage 1310. In one embodiment, computer readable instructions to implement one or more embodiments provided herein may be in storage 1310. Storage 1310 may also store other computer readable instructions to implement an operating system, an application program, and the like. Computer readable instructions may be loaded in memory 1308 for execution by processing unit 1306, for example.

The term "computer readable media" as used herein includes computer storage media. Computer storage media includes volatile and nonvolatile, removable and non-removable media implemented in any method or technology for storage of information such as computer readable instructions or other data. Memory 1308 and storage 1310 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 1302. Any such computer storage media may be part of device 1302.

Device 1302 may also include communication connection(s) 1316 that allows device 1302 to communicate with other devices. Communication connection(s) 1316 may include, but is not limited to, a modem, a Network Interface Card (NIC), an integrated network interface, a radio frequency transmitter/receiver, an infrared port, a USB connection, or other interfaces for connecting computing device 1302 to other computing devices. Communication connection(s) 1316 may include a wired connection or a wireless connection. Communication connection(s) 1316 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 1302 may include input device(s) 1314 such as keyboard, mouse, pen, voice input device, touch input device, infrared cameras, video input devices, and/or any other input device. Output device(s) 1312 such as one or more displays, speakers, printers, and/or any other output device may also be included in device 1302. Input device(s) 1314 and output device(s) 1312 may be connected to device 1302 via a wired connection, wireless connection, or any combination thereof. In one embodiment, an input device or an output device from another computing device may be used as input device(s) 1314 or output device(s) 1312 for computing device 1302.

Components of computing device 1302 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 1302 may be interconnected by a network. For example, memory 1308 may be comprised of multiple physical memory units located in different physical locations interconnected by a network.

Those skilled in the art will realize that storage devices utilized to store computer readable instructions may be distributed across a network. For example, a computing device 1320 accessible via network 1318 may store computer readable instructions to implement one or more embodiments provided herein. Computing device 1302 may access computing device 1320 and download a part or all of the computer readable instructions for execution. Alternatively, computing device 1302 may download pieces of the computer readable instructions, as needed, or some instructions may be executed at computing device 1302 and some at computing device 1320.

G. Usage of Terms

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "example" is used herein to mean serving as an example, instance, or illustration. Any aspect or design described herein as "example" is not necessarily to be construed as advantageous over other aspects or designs. Rather, use of the word example is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method of facilitating a user traveling a path between a first location and a second location and having at least two lanes, the method using a device having a processor and comprising:
  executing on the processor instructions that cause the device to:
    for respective lanes of the path, receive from a travel service a predicted travel duration of the lane between the first location and the second location, wherein:
      the predicted travel duration is based on a travel condition of the lane; and
      at least one lane is associated with a lane cost for users traveling in the lane;
    compare the predicted travel durations of the lanes of the path to identify a selected lane that presents a comparative advantage for a selected travel condition over other lanes of the path, wherein identifying the selected lane comprises:
      comparing the predicted travel durations of the lanes of the path with lane costs of the lanes to identify the selected lane;
    choose a presentation condition to advise the user to choose the selected lane; and responsive to occurrence of the presentation condition, advise the user to choose the selected lane while traveling the path between the first location and the second location.

2. The method of claim 1, wherein:
at least one lane is associated with a lane restriction for users traveling in the lane;
the execution of the instructions on the processor further causes the device to, for the respective lanes, determine whether the user satisfies the lane restriction of the lane; and
identifying the selected lane further comprises: comparing the predicted travel durations of the lanes of the path for which the user satisfies the lane restriction of the lane to identify the selected lane.

3. The method of claim 1, wherein:
the user has a cost sensitivity; and
identifying the selected lane further comprises: comparing the predicted travel durations of the lanes of the path with the lane costs of the lanes and the cost sensitivity of the user to identify the selected lane.

4. The method of claim 3, wherein the execution of the instructions on the processor further causes the device to:
monitor a driving behavior of the user to detect at least one lane selection by the user of a second lane having a second lane cost; and
based on the at least one lane selection by the user and the second lane cost of the second lane, determine the cost sensitivity of the user.

5. The method of claim 4, wherein determining the cost sensitivity of the user comprises:
presenting to the user a presentation including a first lane cost of a first lane and a predicted travel lane duration reduction as compared with another lane; and
detecting a lane selection of the user in response to the presentation.

6. The method of claim 1, wherein:
choosing the presentation condition comprises: choosing a presentation time at which to advise the user to choose the selected lane; and
advising the user comprises: responsive to detecting an arrival of the presentation time, advising the user to choose the selected lane while traveling the path between the first location and the second location.

7. The method of claim 1, wherein:
choosing the presentation condition comprises: choosing a presentation location along the path at which to advise the user to choose the selected lane; and
advising the user comprises: responsive to detecting an arrival of the user at the presentation location along the path, advising the user to choose the selected lane while traveling the path between the first location and the second location.

8. The method of claim 1, wherein:
choosing the presentation condition comprises: identifying a user behavior for which the user is to be advised to choose the selected lane; and
advising the user comprises:
detecting an occurrence of the user behavior; and
responsive to the occurrence of the user behavior, advising the user to choose the selected lane while traveling the path between the first location and the second location.

9. A method of providing a travel service to users respectively traveling on a path, the method using a device having a processor and comprising:
executing on the processor instructions that cause the device to:
upon receiving from a first user a travel report indicating a travel condition for a lane of a path between a first location and a second location during a period, store the travel report;
for respective lanes of the path between the first location and the second location, determine, for respective periods, a typical travel duration for the lane according to travel conditions during the period and a typical travel condition for the lane of the path; and
upon receiving from a second user a request for one or more predicted travel durations of a selected lane of the path during a selected period, provide a predicted travel duration based on the typical travel duration for the selected lane of the path during the selected period and a presentation condition to advise the second user to choose the selected lane while traveling in the selected lane of the path, wherein providing the predicted travel duration for the selected lane comprises:
identifying a lane condition of the selected lane of the path between the first location and the second location during the selected period; and
providing the predicted travel duration based on the lane condition and the typical travel duration for the selected lane of the path during the selected period.

10. The method of claim 9, wherein:
the travel report received from the first user specifies at least one intermediate location of the first user while traveling the path between the first location and the second location; and
executing the instructions on the processor further causes the device to determine, from the at least one intermediate location, the lane of the path of the first user while traveling the path between the first location and the second location.

11. The method of claim 9, wherein:
executing the instructions on the processor further causes the device to:
determine, for respective first users of a first user set traveling the path between the first location and the second location during the period, a travel duration of the first user;
generate a histogram of travel durations of the first users of the first user set;
identify an arithmetic mean of the travel durations of the histogram; and
associate the arithmetic mean of the travel duration with the lane of the path between the first location and the second location during the period; and
determining the typical travel durations of the respective lanes of the path comprises:
selecting the travel duration associated with the lane of the path between the first location and the second location during the period.

12. The method of claim 9, wherein:
the travel report indicates a speed of the first user while traveling the lane of the path between the first location and the second location; and
determining the typical travel durations of the respective lanes of the path comprises: estimating the typical travel duration of the lane according to speeds of users of a first user set, including the first user, users traveling the lane of the path between the first location and the second location during the period.

13. The method of claim 9, wherein determining the typical travel duration of a lane of the path comprises: among travel durations of users of a first user set, including the first user, traveling the lane of the path between the first location and the second location during the period, selecting a shortest travel duration.

14. The method of claim 9, wherein determining the typical travel duration of a lane of the path comprises: among travel durations of users of a first user set, including the first user, traveling the lane of the path between the first location and the second location during the period, selecting an average travel duration.

15. The method of claim 9, wherein determining the typical travel duration of a lane of the path comprises: among travel durations of users of a first user set, including the first user, traveling the lane of the path between the first location and the second location during the period, selecting a longest travel duration.

16. A method of providing a travel service to users respectively traveling on a path, the method using a device having a processor and comprising:
  executing on the processor instructions that cause the device to:
    upon receiving from a first user a travel report indicating a travel condition for a lane of a path between a first location and a second location during a period, store the travel report;
    for respective lanes of the path between the first location and the second location, determine, for respective periods, a typical travel duration for the lane according to travel conditions during the period and a typical travel condition for the lane of the path, wherein determining the typical travel duration of a lane of the path comprises:
      among travel durations of users of a first user set, including the first user, traveling the lane of the path between the first location and the second location during the period, selecting at least one of a shortest travel duration, an average travel duration, or a longest travel duration; and
    upon receiving from a second user a request for one or more predicted travel durations of a selected lane of the path during a selected period, provide a predicted travel duration based on the typical travel duration for the selected lane of the path during the selected period and a presentation condition to advise the second user to choose the selected lane while traveling in the selected lane of the path.

17. The method of claim 16, wherein determining the typical travel duration of a lane of the path comprises: among the travel durations of the users of the first user set, including the first user, traveling the lane of the path between the first location and the second location during the period, selecting the shortest travel duration.

18. The method of claim 16, wherein determining the typical travel duration of a lane of the path comprises: among the travel durations of the users of the first user set, including the first user, traveling the lane of the path between the first location and the second location during the period, selecting the average travel duration.

19. The method of claim 16, wherein determining the typical travel duration of a lane of the path comprises: among the travel durations of the users of the first user set, including the first user, traveling the lane of the path between the first location and the second location during the period, selecting the longest travel duration.

20. A method of providing a travel service to users respectively traveling on a path, the method using a device having a processor and comprising:
  executing on the processor instructions that cause the device to:
    upon receiving from a user a travel report indicating a travel condition for a lane of a path between a first location and a second location during a period, store the travel report;
    determine, for respective first users of a first user set, including the user, traveling the path between the first location and the second location during the period, a travel duration of the first user;
    generate a histogram of the travel durations of the first users of the first user set;
    identify an arithmetic mean of the travel durations of the histogram;
    associate the arithmetic mean of the travel duration with the lane of the path between the first location and the second location during the period;
    for respective lanes of the path between the first location and the second location, determine, for respective periods, a typical travel duration for the lane according to travel conditions during the period and a typical travel condition for the lane of the path, wherein determining the typical travel durations of the respective lanes of the path comprises:
      selecting the travel duration associated with the lane of the path between the first location and the second location during the period; and
    upon receiving from a second user a request for one or more predicted travel durations of a selected lane of the path during a selected period, provide a predicted travel durations based on the typical travel duration for the selected lane of the path during the selected period and a presentation condition to advise the second user to choose the selected lane while traveling in the selected lane of the path.

* * * * *